US012690754B2

(12) United States Patent
Castano Galindo et al.

(10) Patent No.: US 12,690,754 B2
(45) Date of Patent: Jul. 28, 2026

(54) ENDOSCOPY DEVICE HAVING A PUSH-BUTTON BRAKE AND STABILIZATION MECHANISM

(71) Applicant: EvoEndo, Inc., Centennial, CO (US)

(72) Inventors: David Castano Galindo, Fort Lauderdale, FL (US); Blake Monjar, Pompano Beach, FL (US); Damian Tomlin, Coral Springs, FL (US); Paul Imaoka, Jacksonville, FL (US); Joel Friedlander, Englewood, CO (US)

(73) Assignee: EvoEndo, Inc., Centennial, CO (US)

( * ) Notice: Subject to any disclaimer, the term of this patent is extended or adjusted under 35 U.S.C. 154(b) by 38 days.

(21) Appl. No.: 18/927,470

(22) Filed: Oct. 25, 2024

(65) Prior Publication Data

US 2026/0114721 A1 Apr. 30, 2026

(51) Int. Cl.
| | |
|---|---|
| *A61B 1/005* | (2006.01) |
| *A61B 1/00* | (2006.01) |
| *A61B 1/233* | (2006.01) |

(52) U.S. Cl.
CPC ........ *A61B 1/0052* (2013.01); *A61B 1/00066* (2013.01); *A61B 1/233* (2013.01)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS

| | | | | |
|---|---|---|---|---|
| 4,942,866 A | * | 7/1990 | Usami ................ | G02B 23/2476 |
| | | | | 600/148 |
| 5,014,685 A | * | 5/1991 | Takahashi ......... | A61M 25/0136 |
| | | | | 600/148 |

(Continued)

FOREIGN PATENT DOCUMENTS

| | | | |
|---|---|---|---|
| JP | 2012231884 A | * | 11/2012 |
| JP | 2013005996 A | * | 1/2013 |

OTHER PUBLICATIONS

International Search Report and Written Opinion; International Application No. PCT/US2025/052548; Feb. 24, 2026.

*Primary Examiner* — Ryan N Henderson
(74) *Attorney, Agent, or Firm* — Farber LLC

(57) ABSTRACT

Systems and methods are disclosed for an endoscope for use in a surgical procedure, e.g., a pediatric trans-nasal endoscopy procedure. The endoscope may include a handle for gripping by a user, and a shaft extending from the handle. The shaft may have a working channel extending longitudinally therethrough and a distal region configured to be inserted into a patient. The endoscope may also include a steering wire extending longitudinally through the shaft from the distal region of the shaft to the steering control mechanism of the handle. The steering control mechanism may have an actuation mechanism attached to the steering wire. The endoscope may include a steering tension braking feature that enables selective engagement and disengagement by the user to brake the steering tension force on the steering wire. The endoscope may also have a steering wire slack reduction member configured to reduce unintended slack from forming along the steering wires during use. The endoscope may also have a steering wire resting tension adjustment mechanism configured to adjust a resting tension on the steering wire prior to the user tensioning the steering wire during a surgical operation.

7 Claims, 19 Drawing Sheets

(58) Field of Classification Search
CPC ... A61B 1/0056; A61B 1/0057; A61B 1/0058;
A61B 1/00066; A61B 1/003; A61B
1/00318; A61B 1/00323; A61M 25/0133;
A61M 25/0136; A61M 25/0147
See application file for complete search history.

(56) References Cited

U.S. PATENT DOCUMENTS

| | | | | |
|---|---|---|---|---|
| 5,888,192 | A * | 3/1999 | Heimberger | G02B 23/2476 |
| | | | | 600/146 |
| 9,636,481 | B2 * | 5/2017 | Campbell | A61M 25/0147 |
| 10,357,633 | B2 * | 7/2019 | Campbell | A61B 1/0051 |
| 11,324,394 | B2 * | 5/2022 | Rask | A61B 1/05 |
| 11,642,496 | B2 * | 5/2023 | Campbell | A61M 25/0136 |
| | | | | 604/95.04 |
| 11,931,530 | B2 * | 3/2024 | Campbell | A61B 1/0057 |
| 12,097,341 | B2 * | 9/2024 | Campbell | A61B 1/0057 |
| 12,337,124 | B2 * | 6/2025 | Campbell | A61M 25/0147 |
| 2001/0037051 | A1 | 11/2001 | Fujii et al. | |
| 2004/0059191 | A1 * | 3/2004 | Krupa | A61M 25/0136 |
| | | | | 600/146 |
| 2009/0124398 | A1 * | 5/2009 | Thompson | A61B 1/0052 |
| | | | | 464/52 |
| 2011/0213300 | A1 | 9/2011 | McWeeney et al. | |
| 2014/0088497 | A1 * | 3/2014 | Campbell | A61M 25/0136 |
| | | | | 604/95.04 |
| 2015/0351610 | A1 * | 12/2015 | Fan | A61B 1/0052 |
| | | | | 600/148 |
| 2017/0203078 | A1 * | 7/2017 | Campbell | A61B 1/0052 |
| 2018/0028048 | A1 * | 2/2018 | Simmons | A61M 25/0105 |
| 2019/0290886 | A1 * | 9/2019 | Campbell | A61B 1/0051 |
| 2022/0151463 | A1 | 5/2022 | Fancher et al. | |
| 2022/0354346 | A1 * | 11/2022 | Kefurt | A61B 1/0008 |
| 2023/0219212 | A1 * | 7/2023 | Kawakami | A61B 1/0052 |
| | | | | 74/500.5 |
| 2023/0233807 | A1 * | 7/2023 | Campbell | A61B 1/0051 |
| | | | | 604/95.04 |
| 2023/0293852 | A1 * | 9/2023 | Campbell | A61B 1/0057 |
| | | | | 604/95.04 |
| 2023/0389785 | A1 * | 12/2023 | Inoue | A61B 1/0052 |
| 2024/0016369 | A1 * | 1/2024 | Christensen | A61B 1/0052 |
| 2024/0181217 | A1 * | 6/2024 | Campbell | A61M 25/0147 |
| 2025/0050068 | A1 * | 2/2025 | Campbell | A61B 1/0051 |

* cited by examiner

ENDOSCOPY DEVICE HAVING A PUSH-BUTTON BRAKE AND STABILIZATION MECHANISM

BACKGROUND

Eosinophilic esophagitis (EoE) is an increasingly common chronic inflammatory disease that affects children and adults. Because of its potential to progress to esophageal stricture and the fact that symptoms do not always correlate with degree of eosinophilia, much attention has been paid to repeated assessment of the esophageal mucosa to ensure mucosal healing following treatment. In contrast, the risks, cost and time commitment associated with traditional sedated esophagogastroduodenoscopy (EGD) can be significant and have raised concerns for providers and patients alike. To address these questions, alternative methods are needed to measure esophageal inflammation. In addition to esophagoscopy with biopsies, other technologies such as the Cytosponge, esophageal string test and confocal tethered endomicroscopy have emerged as potential alternatives for assessing mucosal inflammation.

Recent work has led to the development of trans-nasal endoscopy/esophagoscopy (TNE) to assess the esophageal mucosa in adults. In contrast to traditional EGDs, TNE offers advantages, including that it can be performed in an outpatient clinic room, requires no anesthesia or sedation, uses an adult trans-nasal gastroscope that is tolerated by adults and procures samples adequate for assessment of Barrett's Esophagus. However, the endoscopes used in the adult procedures are not appropriate for use in pediatric setting and, in fact, may be too large for many adults.

During a trans-nasal endoscopic procedure, patients may experience physical discomfort due to the endoscope being inserted into the nose, through the sinus cavities and down into the esophagus. This physical discomfort, or even the fear of being uncomfortable, can make trans-nasal endoscopy procedures mentally and emotionally distressing for a patient, too. Because it is desirable to make the procedure mentally and physically easier on the patient, it would be advantageous to optimize the endoscope being used for the procedure.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The trans-nasal endoscope described hereinbelow, according to various embodiments, addresses various challenges. For example, the trans-nasal endoscope described hereinbelow, according to various embodiments, provides a device and associated methodology that can be used to adapt TNE to assess the esophageal mucosa, gastric, and duodenal, tracheal, and bronchial mucosa in children and small adults in both a sedated and unsedated/sedation-free manner with a full array of steering and visualization capabilities. The trans-nasal endoscope described hereinbelow, according to various embodiments, provides a scope that minimizes the outer diameter thereof, e.g., to reduce the discomfort to patients, while maximizing the diameter of the working channel, e.g., to provide the largest possible channel through which tools may be introduced, while simultaneously providing enhanced, e.g., four-way, steering capabilities as well as visualization functionality, as will be described more fully below. In various embodiments, the outer diameter of the endoscope shaft may be less than about 4.5 mm, and preferably is about 3.5 mm. In addition, in various embodiments, the diameter of the working channel may have a range of about 1.5 mm to 2.5 mm, and preferably is about 2.0 mm. In certain embodiments, the outer diameter of the endoscope shaft may be between about 4.3 to 4.5 mm, and the diameter of the working channel may be about 2.8 mm.

It is noted that, according to various embodiments, the endoscope described herein may be particularly well-suited for unsedated/sedation-free (these terms used interchangeably herein) surgical procedures. Sedation is well-known, in certain circumstances, to present various risks to patients, but is often employed during surgical procedures to prevent a patient from experiencing discomfort or anxiety. By providing an endoscope having, e.g., a minimized outer diameter, a more flexible and more steerable distal regions (as will be explained in further detail below) among other advantages described below, patient discomfort and anxiety may be reduced, thereby enabling surgical procedures to be performed in an unsedated/sedation-free, and thus more safe, manner.

It should be recognized that, while the scope set forth herein is described hereinbelow for use in a trans-nasal endoscopy procedure, it may also be employed in a variety of other medical or surgical applications. For example, the scope set forth herein may be employed for use as a nasal endoscope, a trans-nasal esophagoscope, a trans-nasal gastroscope, a trans-nasal duodenoscope, a trans-nasal enteroscope, a triple endoscope, a bronchoscope, a laryngoscope, a trans-nasal gastroscope, an aerodigestive scope, and/or an endoscopic device used to visualize any body cavity into which it would fit, e.g., for examination of a stricture or the like. It should also be recognized that the endoscope described herein may be employed in fetal surgical procedures, and/or in surgical procedures that employ natural orifices, e.g., NOTES or natural orifice transluminal endoscopic procedures, such as trans-orally, trans-anally, trans-vaginally or any other natural orifice. The discussion herein of a pediatric trans-nasal endoscopy procedure is merely exemplary.

In accordance with various embodiments thereof, systems and methods are provided for use in a surgical procedure. In an embodiment, there is provided an endoscope for use in a surgical procedure, e.g., a pediatric trans-nasal endoscopy procedure, that includes a handle for gripping by a user, the handle having a steering control mechanism. The endoscope may also include a shaft extending from the handle, the shaft having a distal region configured to be inserted into a patient. In addition, the endoscope may have a steering wire extending longitudinally through the shaft from the distal region of the shaft to the steering control mechanism of the handle. The steering control mechanism may include a first actuation mechanism attached to the steering wire. The steering control mechanism may also include a tensioning feature that enables the first actuation mechanism to generate a resting tension force on the steering wire prior to the first actuation mechanism being actuated, e.g., during a manufacturing process or the like. The first actuation mechanism may be subsequently actuatable by a user, e.g., during the surgical procedure, to generate a steering tension force on the steering wire so as to steer the distal region of the shaft.

In embodiments, the tensioning feature may include ratchet teeth that enable the first actuation mechanism to be rotated relative to the handle in a first rotational direction but that prevent rotation of the first actuation mechanism relative to the handle in the opposite rotational direction, so as to maintain the resting tension force on the steering wire prior to the first actuation mechanism being actuated. The first actuation mechanism may include a roller wheel located within the handle. The first actuation mechanism may also include a roller knob located outside of the handle and attached to the roller wheel. The roller knob may be graspable and rotatable by a user to actuate the roller wheel. The ratchet teeth may be positioned on a side wall of the roller wheel.

In various embodiments, the endoscope may also include a second steering wire extending longitudinally through the shaft from the distal region of the shaft to the steering control mechanism of the handle. The steering control mechanism may include a second roller wheel within an opposite side of the handle and attached to the second steering wire, the first and second roller wheels actuatable by the user, e.g., during the surgical procedure, to generate steering tension forces in opposite longitudinal directions on their respective steering wires so as to control steering of the distal region of the shaft in the left and right directions.

In still further embodiments, the endoscope may include third and fourth steering wires extending longitudinally through the shaft from the distal region of the shaft to the steering control mechanism of the handle. The steering control mechanism may include third and fourth roller wheels attached to the third and fourth steering wires respectively. The third and fourth roller wheels may be actuatable by the user, e.g., during the surgical procedure, to generate steering tension forces in opposite longitudinal directions on their respective steering wires so as to control steering of the distal region of the shaft in the up and down directions. The third and fourth roller wheels may be attached to a thumb knob extending through a slot at the proximal end of the handle.

Additionally, the endoscope may include a steering collar located at the distal region of the shaft. The steering wires may be connected to the steering collar at circumferentially spaced apart locations such that the steering wires being pulled by their respective actuators selectively move such locations of the steering collar to steer the distal region of the shaft.

In accordance with other embodiments, there may be provided an endoscope for use in a surgical procedure. The endoscope may include a handle for gripping by a user. The handle may have a steering control mechanism. The endoscope may also include a shaft extending from the handle, the shaft having a distal region configured to be inserted into a patient. In addition, the endoscope may include a steering wire extending longitudinally through the shaft from the distal region of the shaft to the steering control mechanism of the handle. The steering control mechanism may include a first actuation mechanism attached to the steering wire. The steering control mechanism may include a resting tension feature that enables the first actuation mechanism to generate and maintain a resting tension on the steering wire prior to the first actuation mechanism being actuated during the surgical procedure, e.g., during a manufacturing process or the like. The steering control mechanism may also include a resting tension adjustment feature that enables selective engagement and disengagement of the resting tension feature so as to enable the resting tension force on the steering wire to be adjusted.

In embodiments, the first actuation mechanism may include a roller wheel and the resting tension feature may include a set of ratchet teeth on a side wall of the roller wheel. The set of ratchet teeth may enable the first actuation mechanism to be rotated relative to the handle in a first rotational direction but prevent rotation of the first actuation mechanism relative to the handle in the opposite rotational direction, so as to maintain the resting tension force on the steering wire prior to the first actuation mechanism being actuated by a user during the surgical procedure. The resting tension adjustment feature may include a spacer selectively positionable adjacent to the first actuation mechanism.

In various embodiments, when the spacer is positioned adjacent to the first actuation mechanism, the spacer maintains the ratchet teeth in engagement with, e.g., a feature of the handle or a roller knob, etc., so as to maintain the resting tension on the steering wire prior to the first actuation mechanism being actuated during the surgical procedure. In addition, in embodiments, when the spacer is not positioned adjacent to the first actuation mechanism, e.g., when the spacer is removed therefrom, the ratchet teeth may be disengageable from the handle so as to enable the resting tension on the steering wire to be adjusted prior to the first actuation mechanism being actuated during the surgical procedure.

The first actuation mechanism may be subsequently actuatable by a user, e.g., during the surgical procedure, to generate a steering tension force on the steering wire so as to steer the distal region of the shaft. In embodiments, the first actuation mechanism may include a roller wheel located within the handle and a roller knob located outside of the handle and attached to the roller wheel. The roller knob may be graspable and rotatable by a user during a surgical procedure to actuate the roller wheel.

In various embodiments, the endoscope may also include a second steering wire extending longitudinally through the shaft from the distal region of the shaft to the steering control mechanism of the handle. The steering control mechanism may include a second roller wheel within an opposite side of the handle and attached to the second steering wire. The first and second roller wheels may be subsequently actuatable by the user, e.g., during the surgical procedure, to generate steering tension forces in opposite longitudinal directions on their respective steering wires so as to control steering of the distal region of the shaft in the left and right directions.

In still further embodiments, the endoscope may also include third and fourth steering wires extending longitudinally through the shaft from the distal region of the shaft to the steering control mechanism of the handle. The steering control mechanism may include third and fourth roller wheels attached to a thumb knob extending through a slot at the proximal end of the handle. The third and fourth roller wheels may be attached to the third and fourth steering wires respectively. The third and fourth roller wheels may be actuatable by the user to generate steering tension forces in opposite longitudinal directions on their respective steering wires so as to control steering of the distal region of the shaft in the up and down directions. In embodiments, the endoscope may also include a steering collar located at the distal region of the shaft. The steering wires may be connected to the steering collar at circumferentially spaced apart locations such that the steering wires being pulled by their respective actuators selectively move such locations of the steering collar to steer the distal region of the shaft.

According to still further embodiments, there is also provided an endoscope for use in a surgical procedure that includes a handle for gripping by a user, the handle having a steering control mechanism. The endoscope may also have a shaft extending from the handle, the shaft having a distal region configured to be inserted into a patient. The endoscope may also include a steering control mechanism on the handle. In embodiments, the steering control mechanism may include a shaft extending laterally through the handle, and a roller wheel located within the handle and rotatable about the shaft. The steering control mechanism have also include a roller knob located outside of the handle, the roller knob graspable and rotatable by a user during a surgical procedure to rotate the roller wheel and thereby actuate the steering mechanism. Each of the roller knob and the shaft may have a rotational mating feature such that the shaft rotates when the roller knob is rotated. In addition, each of the roller knob and the shaft may have a lateral mating feature which maintains the roller knob on the shaft and maintains the roller knob in engagement with the roller wheel.

In embodiments, the rotational mating feature of the shaft and the roller knob may be flat regions along their respective cross sections that prevent the roller knob from rotating relative to the shaft. The lateral mating feature of the shaft may be a void in the surface of the shaft and the lateral mating feature of the roller knob may be a protuberance that fits into the void on the shaft (or vice versa). The roller knob may be configured to be press-fit onto the shaft so as to engage the rotational and lateral mating features of the shaft and the roller knob.

The roller wheel and the roller knob may also have rotational locking features that engage each other when the rotational and lateral mating features of the shaft and the roller knob are engaged. In embodiments, the rotational locking features of the roller wheel and the roller knob may be respective sets of ratchet teeth located on the roller wheel and the roller knob. In addition, the steering control mechanism may also include a spacer within the handle. The spacer may be selectively positionable adjacent to the roller wheel such that, when the spacer is positioned adjacent to the roller wheel, the spacer maintains the ratchet teeth of the roller wheel and the roller knob in engagement with each other, and when the spacer is not positioned adjacent to the roller wheel, the ratchet teeth of the roller wheel and the roller knob are disengagable from each other.

In further embodiments, the steering control mechanism may include a steering wire connected to the roller wheel and which may be configured to be pulled longitudinally when a user rotates the roller wheel via the roller knob. The steering control mechanism may also include a second roller wheel located within an opposite side of the handle, a second roller knob located outside of the opposite side of the handle, and a second steering wire connected to the second roller wheel and configured to be pulled longitudinally when a user rotates the second roller wheel via the second roller knob. The steering control mechanism may also include a steering collar located at a distal region of the shaft, the first and second steering wires connected to the steering collar such that longitudinal pulling of the steering wires causes the steering collar to move and thereby steer the distal region of the shaft.

In still further embodiments, there is provided an endoscope for use in a surgical procedure, comprising a handle for gripping by a user, the handle having a steering control mechanism. The endoscope also includes a shaft extending from the handle, the shaft having a distal region configured to be inserted into a patient. The endoscope also includes a steering wire extending longitudinally through the shaft from the distal region of the shaft to the steering control mechanism of the handle, the steering control mechanism including a first actuation mechanism attached to the steering wire, the first actuation mechanism actuatable by a user during the surgical procedure to generate a steering tension force on the steering wire so as to steer the distal region of the shaft. The steering control mechanism may include a steering tension braking feature that enables selective engagement and disengagement by the user to brake the steering tension force on the steering wire. The steering tension braking feature may prevent the shaft from moving after a desired steered position has been achieved.

In embodiments, the steering tension braking feature may include an o-ring selectively pressable into a roller wheel within the handle, the steering wire attached to and actuatable by the roller wheel. The o-ring may reside within an o-ring retention member that is movable radially inwardly and outwardly relative to the handle. The steering tension braking feature may include a user-actuatable button having a radially-inwardly extending finger that engages the o-ring retention member. The o-ring retention member may be biased radially outwardly by a spring such that, in a resting position when the button is not pressed, the spring maintains the o-ring spaced apart from the roller wheels such that the steering wire is not braked.

In embodiments, in an actuated position with the button pressed, a force of the spring maintains may be overcome such that the o-ring presses against the roller wheels such that the steering wire is braked. The steering tension braking member may be selectively lockable and unlockable via a brake holding mechanism. The brake holding mechanism may include a flexible annular lip that engages a complementary annular lip on the handle. The brake holding mechanism may include an annular thread that engages a complementary annular thread on the handle.

In still further embodiments, there is provided an endoscope for use in a surgical procedure. The endoscope may include a handle for gripping by a user, the handle having a steering control mechanism. The endoscope may also include a shaft extending from the handle, the shaft having a distal region configured to be inserted into a patient. The endoscope may also include a steering wire extending longitudinally through the shaft from the distal region of the shaft to the steering control mechanism of the handle, the steering control mechanism including a first actuation mechanism attached to the steering wire, the first actuation mechanism actuatable by a user during the surgical procedure to generate a steering tension force on the steering wire so as to steer the distal region of the shaft. The endoscope may further include a steering wire slack reduction member configured to reduce unintended slack from forming along the steering wires during use.

In embodiments, the steering wire slack reduction member may maintain additional tension on the steering wires while the steering wires are being operated by the user. The steering wire slack reduction member may be formed of a flexible material which flexes when the steering wires are under tension to maintain the additional tension on the steering wires while the steering wires are being operated by the user. The flexible material may flex longitudinally when the steering wires are under tension to maintain the additional tension on the steering wires while the steering wires are being operated by the user. Additionally or alternatively, the flexible material may flex radially when the steering wires are under tension to maintain the additional tension on the steering wires while the steering wires are being operated by the user. In embodiments, the flexible material may be silicone. The steering wire slack reduction member may define one or more of through-holes, slits or indentations which are engaged by the steering wires. The steering wires may be fixed to the steering wire slack reduction member, or the steering wires may be slidable relative to the steering wire slack reduction member.

In additional embodiments, there is provided an endoscope for use in a surgical procedure, which includes a handle for gripping by a user, the handle having a steering control mechanism; a shaft extending from the handle, the shaft having a distal region configured to be inserted into a patient; a steering wire extending longitudinally through the shaft from the distal region of the shaft to the steering control mechanism of the handle, the steering control mechanism including a first roller wheel attached to the steering wire, the first roller wheel configured to steer the distal region of the shaft with the steering wire during a surgical procedure in response to the user operating the steering control mechanism. The endoscope may also include a steering wire resting tension adjustment mechanism configured to adjust a resting tension on the steering wire prior to the user tensioning the steering wire during a surgical operation.

In embodiments, the steering wire resting tension adjustment mechanism may include a ratchet wheel rotatably mounted on and relative to the roller wheel. The ratchet wheel may be configured to grasp the steering wire and to be rotated to adjust the resting tension on the steering wire prior to the user tensioning the steering wire during a surgical operation. The steering wire resting tension adjustment mechanism may also include a spring, e.g., a leaf spring, mounted on the roller wheel. The ratchet wheel may have ratchet teeth, and the ratchet teeth and the spring may have complementary features that permit the ratchet wheel to be rotated in a first direction relative to the roller wheel and that prevent the ratchet wheel from being rotated relative to the roller wheel in a second direction opposite to the first direction.

In embodiments, the steering control mechanism may include a second roller wheel attached to a second steering wire, the second roller wheel configured to steer the distal region of the shaft with the second steering wire during a surgical procedure in response to the user operating the steering control mechanism, the second roller having a second steering wire resting tension adjustment mechanism configured to adjust a resting tension on the second steering wire prior to the user tensioning the second steering wire during a surgical operation. Additionally or alternatively, the steering control mechanism may also include third and fourth roller wheels attached to respective third and fourth steering wires, the third and fourth roller wheels configured to steer the distal region of the shaft with the third and fourth steering wires during a surgical procedure in response to the user operating the steering control mechanism, each one of the third and fourth roller wheels having a respective third and fourth steering wire resting tension adjustment mechanism configured to adjust a resting tension on the third and fourth steering wires prior to the user tensioning the third and fourth steering wires during a surgical operation.

It should be noted, of course, that to the extent that images, e.g., image signals, image data, etc., are described herein, it will be understood that such also refers to video, e.g., video signals, video data, etc., and that the description of the image signals is intended to include single images, still images, video images, etc. without limitation.

DETAILED DESCRIPTION

Reference will now be made in detail to specific embodiments illustrated in the accompanying drawings. In the following detailed description, numerous specific details are set forth to provide a thorough understanding. However, it will be apparent to one of ordinary skill in the art that embodiments may be practiced without these specific details. In other instances, known methods, procedures, components, circuits, and networks have not been described in detail so as not to unnecessarily obscure aspects of the embodiments.

Figure 1:
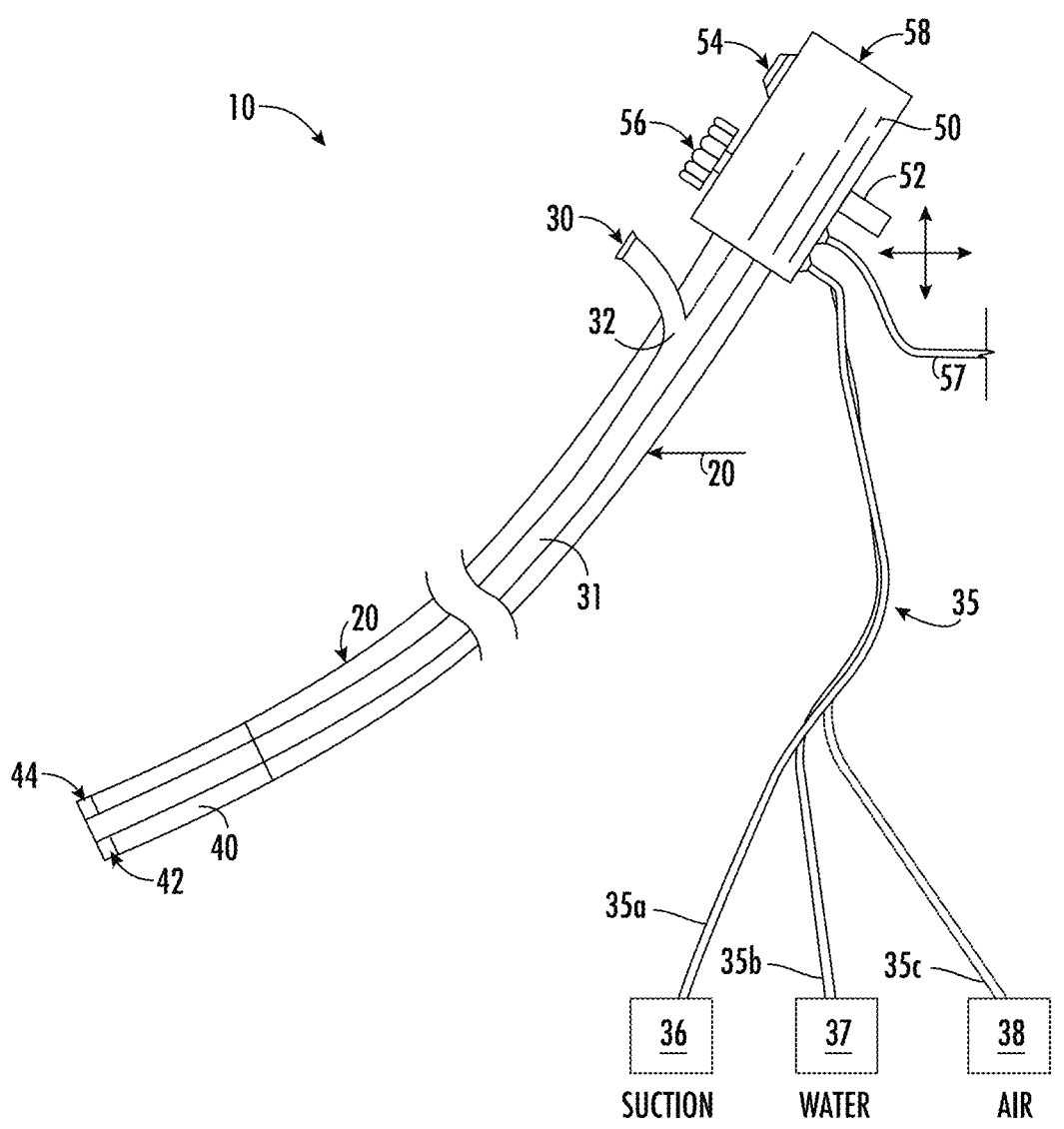
FIG. 1 shows a schematic representation of a trans-nasal endoscope that includes a flexible endoscope shaft, in accordance with various embodiments.

FIG. 1 is a schematic diagram of a trans-nasal endoscope 10, according to one example embodiment, illustrating some of the various features thereof. As mentioned previously, while the example embodiments set forth hereinbelow are described as an endoscope that is suitable for trans-nasal insertion into a patient, and is particularly well-suited for unsedated/sedation-free trans-nasal insertion into a child or small adult, it is understood that this is merely one example embodiment, and that the description hereinbelow of a trans-nasal endoscope does not preclude the use of the device in other types of procedures and for other types of patients. It should be noted that FIG. 1 is merely schematic, and thus the shape and position of the various features illustrated therein are merely exemplary. Additional figures, illustrating specific embodiments of the various features and functionality, will be provided in further detail below.

In the embodiment shown schematically in FIG. 1, the trans-nasal endoscope 10 includes a flexible endoscope shaft 20. The flexible endoscope shaft 20 has a working channel 31. The working channel 31 extends longitudinally from a distal end 40 of the endoscope shaft 20 proximally towards a handle 50 located at or near the proximal end of the trans-nasal endoscope 10. At, within or near the handle 50, the working channel 31 has a bifurcation region 32. Proximal to the bifurcation region 32, the working channel 31 splits into two channels. A first portion of the working channel 31 proximal to the bifurcation regions 32 extends towards an instrument insertion port 30 suitable for, e.g., conducting a biopsy therethrough. The instrument insertion port 30 allows an instrument, e.g., a pediatric nasal endoscope biopsy forceps or other medical device, to be inserted through the bifurcation region 32 and to, and past, the distal end 40 of the endoscope shaft 20 so as to perform a procedure, e.g., a biopsy procedure, on tissue located at or near to the distal end 40 of the endoscope shaft 20.

A second portion of the working channel 31 proximal to the bifurcation regions 32 extends towards an air, water and suction (AWS) control mechanism 52. The AWS control mechanism 52 includes various valves (not shown in this view, but shown and described more fully in Applicant's co-pending U.S. patent application Ser. No. 18/108,558 filed on Feb. 10, 2023, and in Applicant's co-pending U.S. patent application Ser. No. 63/499,681 filed on May 2, 2023, the disclosure of both being hereby incorporated by reference herein in their entirety) that allow selective connection of the working channel 31 to the AWS tubing set 35. The AWS tubing set 35 may include one or more flexible tubes (shown and described more fully in Applicant's co-pending U.S. patent application Ser. No. 18/108,558, and in Applicant's co-pending U.S. patent application Ser. No. 63/499,681 filed on May 2, 2023). The AWS tubing set 35 may be connected to a water source 37 for supplying water through the working channel 31, to a suction source 36 for supplying suction through the working channel 31, and/or to an air source 38 for supplying air through the working channel 31, depending upon a user's selection via the AWS control mechanism 52. More specifically, the AWS control mechanism allows a user to direct one or more of air, suction or water through, e.g., the bifurcation region 32 and to, and past, the distal end 40 of the endoscope shaft 20 so as to enable their use during the performance of a procedure on tissue located at or near to the distal end 40 of the endoscope shaft 20.

The distal end 40 of the endoscope shaft 20 also includes an illumination source 42 to provide light at the distal tip 40. In embodiments, the illumination source 42 may be connected to and at least partially controllable by an electronics control module 54 located in the handle 50. The distal end 40 of the endoscope shaft 20 also includes an image capture device 44 to convey image or video signals related to the region of the distal end 40 of the endoscope shaft 20. In embodiments, the image capture device 44 may also be connected to and at least partially controllable by the electronics control module 54 located in the handle 50. The handle 50 may also include a shaft steering mechanism 56 to control or steer the lateral displacement at the distal end 40 of the endoscope shaft 20. In addition, the handle 50 may include a video display output cable 57, which may be connected to and output image data to a separate image or video display or control unit (not shown in this view).

Figure 2:
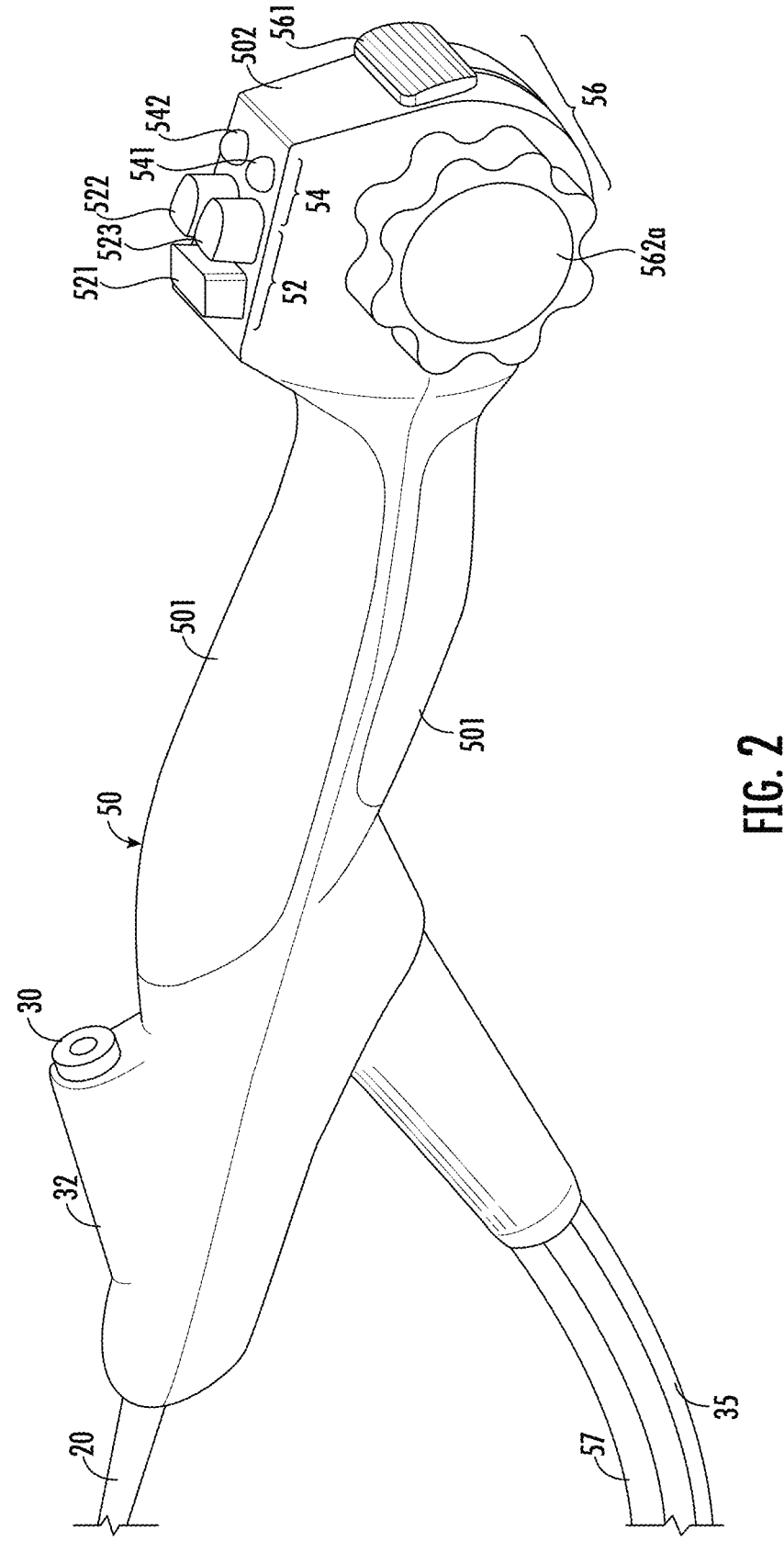
FIG. 2 is a perspective view of the handle of the trans-nasal endoscope, in accordance with various embodiments.

FIG. 2 is a perspective view of an example embodiment of the handle 50 of the trans-nasal endoscope 10. In this embodiment, the features and functionality that were shown schematically in FIG. 1 are provided in more detail, showing additional advantages thereof. For example, in this embodiment, the handle 50 of the trans-nasal endoscope 10 includes a gripping region 501 sized and contoured to fit comfortably in a user's hand. Although shown in FIG. 2 as having a relatively smooth outer surface, the gripping regions 501 may additionally or alternatively have outer surfaces that have features that provide improved grip thereon. For example, the outer surfaces of the gripping regions 501 may include, in certain embodiments, one or more grooves formed therein so as to provide additional gripping purchase when held in the hand of a user. Furthermore, the gripping regions 501, whether having a smooth outer surface or having additional gripping features thereon, may be formed, in some embodiments, of a different, e.g., softer and/or more absorbent, material than the handle 50 so as to provide additional comfort for the user and/or additional absorbency of wet or damp hands of the user.

Located distally relative to the gripping region 501 is the bifurcation region 32. From the distalmost end of the bifurcation region 32 extends the flexible endoscope shaft 20, having a portion of the working channel 31 extending therethrough. The working channel 31 extends from the distal end 40 of the endoscope shaft 20, and splits into two channels in the bifurcation region 32. A first portion of the working channel 31 extends towards the instrument insertion port 30, which is suitable for receiving an instrument, e.g., a pediatric nasal endoscope biopsy forceps or other medical device, therethrough. The second portion of the working channel 31 proximal to the bifurcation region 32 extends proximally through the interior of the gripping region 501.

Proximal to the gripping region 501 is a control region 502 sized and shaped to extend beyond the heel of the user's hand when the palm of the user's hand is gripping the gripping region 501, enabling the control features positioned on the control region 502 to be engaged by the user's second hand when the user's first hand is gripping the gripping region 501.

In the embodiment shown in FIG. 2, the control region 502 has various control features positioned thereon. For example, the control region 502 has the AWS control mechanism 52. As set forth above, the AWS control mechanism 52 includes various features, e.g., buttons, valves, etc., that allow selective connection of the air, water and suction supply sources 36, 37, 38 to the working channel 31 via respective flexible tubes of the AWS tubing set 35. In the embodiment shown in FIG. 2, the AWS control mechanism 52 includes an air supply control button 521. The air supply control button 521 functions to selectively connect the air source 38 to the working channel 31. In the embodiment shown in FIG. 2, the AWS control mechanism 52 also includes a water supply control button 522. The water supply control button 522 functions to selectively connect the water source 37 to the working channel 31. Still further, in the embodiment shown in FIG. 2, the AWS control mechanism 52 includes a suction supply control button 523. The suction supply control button 523 functions to selectively connect the suction source 36 to the working channel 31. The operation of the air, water and suction supply control buttons 521, 522, 523 are shown and described more fully in Applicant's co-pending U.S. patent application Ser. No. 18/108,558, and in Applicant's co-pending U.S. patent application Ser. No. 63/499,681 filed on May 2, 2023.

In the embodiment shown in FIG. 2, the control region 502 also has the electronics control mechanism 54. As set forth above, the electronics control mechanism 54 includes various features, e.g., buttons, electrical connections, etc., that allow selective operation of, e.g, the image capture device 44 and/or the illumination device 44 located at the distal end 40 of the endoscope shaft 20. In the embodiment shown in FIG. 2, the electronics control mechanism 54 includes a first, e.g., a white balance control, button 541. In this embodiment, the white balance control button 541 functions to selectively control a white balancing operation by sending a corresponding signal to an image or video control unit (not shown), as is shown and described more fully in Applicant's co-pending U.S. patent application Ser. No. 18/108,564 filed on Feb. 10, 2023, and in Applicant's co-pending U.S. patent application Ser. No. 63/499,686 filed on May 2, 2023, the disclosure of both being incorporated by reference herein in their entirety.

In the embodiment shown in FIG. 2, the electronics control mechanism 54 also includes a second, e.g., an image capture control, button 542. In this embodiment, the image capture control button 542 functions to selectively control the capture of image or video signals sent by the image capture device 44, e.g., such as by providing a signal to an image or video display or control unit (not shown), as is shown and described more fully in Applicant's co-pending U.S. patent application Ser. No. 18/108,564, and in Applicant's co-pending U.S. patent application Ser. No. 63/499, 686 filed on May 2, 2023.

In the embodiment shown in FIG. 2, the control region 502 also has the shaft steering mechanism 56. As set forth above, the shaft steering mechanism 56 includes various features, e.g., knobs, rollers, etc., that allow a user to control or steer the lateral displacement at the distal end 40 of the endoscope shaft 20. In the embodiment shown in FIG. 2, the shaft steering mechanism 56 includes a first knob 561 for controlling a first movement of the distal end 40 of the endoscope shaft 20, as will be described in greater detail below. FIG. 2 also illustrates the shaft steering mechanism 56 including opposing roller knobs 562a, 562b (knob 562b being hidden from view in FIG. 2, but being located on the opposite side of the handle 50) for controlling additional movements of the distal end 40 of the endoscope shaft 20, as will be described in greater detail below, and certain details of which are shown and described more fully in Applicant's co-pending U.S. patent application Ser. No. 18/108,562 filed on Feb. 10, 2023, the disclosure of which is hereby incorporated by reference herein in its entirety.

In addition, in the embodiment shown in FIG. 2, the handle 50 of the trans-nasal endoscope 10 includes a connection to the AWS tubing set 35. As set forth above, the AWS tubing set includes various flexible tubes that connect to the suction source 36, the water source 37 and the air source 38, as is shown and described more fully in Applicant's co-pending U.S. patent application Ser. No. 18/108, 558, and in Applicant's co-pending U.S. patent application Ser. No. 63/499,681 filed on May 2, 2023. Still further, the handle 50 includes a connection to a video display output 57, e.g., for connecting to and outputting image data to a separate video display or control unit (not shown in FIG. 2). In the embodiment shown in FIG. 2, the video display output 57 is bundled together with the AWS tubing set 35, as is shown and described more fully in Applicant's co-pending U.S. patent application Ser. No. 18/108,564, and in Applicant's co-pending U.S. patent application Ser. No. 63/499, 686 filed on May 2, 2023.

Figure 3:
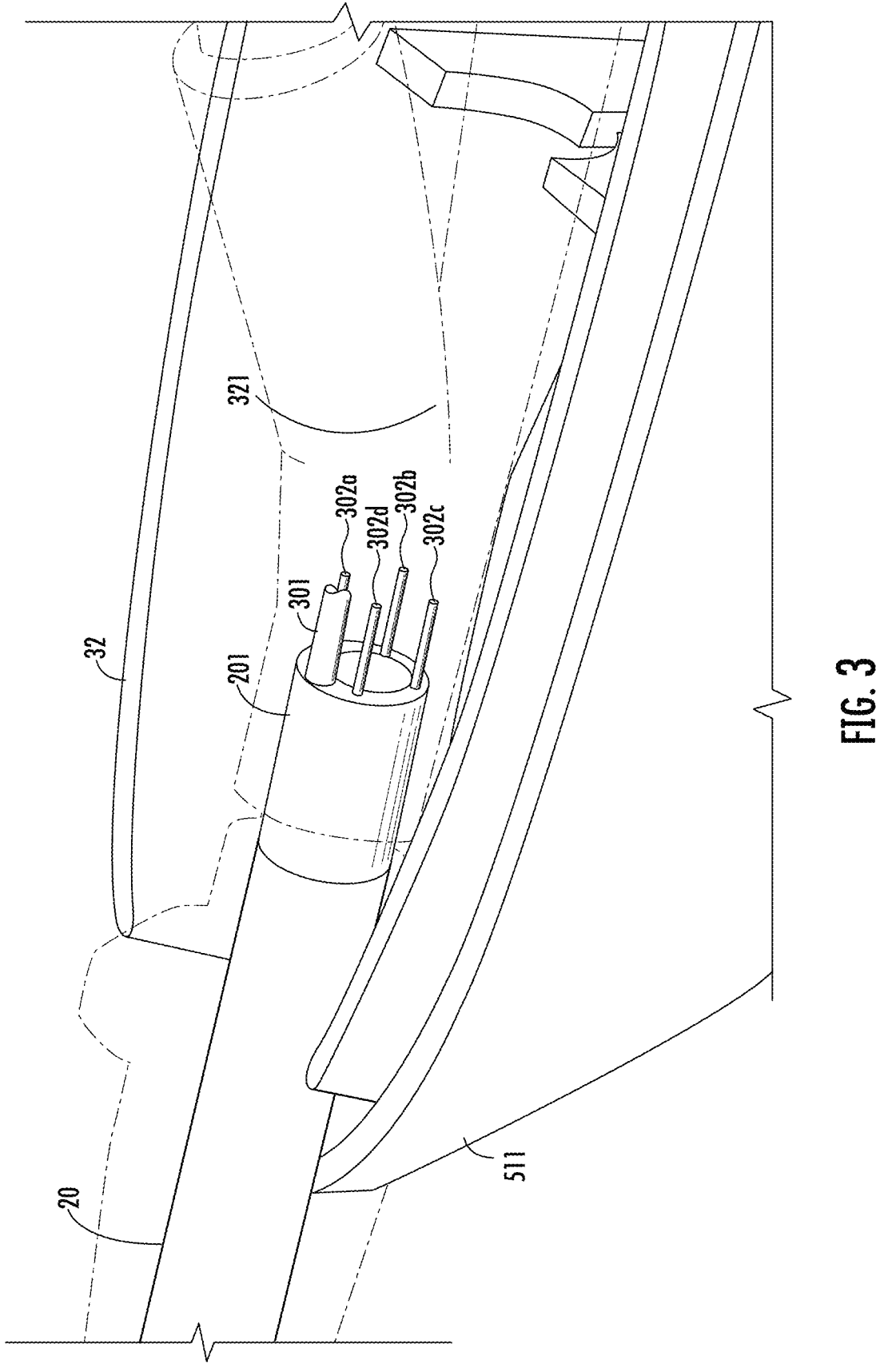
FIG. 3 is a perspective, cut-away view of portions of the handle, in accordance with various embodiments.

FIG. 3 is a perspective, cut-away view of the handle 50 in the vicinity of the bifurcation region 32. In the embodiment shown in FIG. 3, the endoscope shaft 20 terminates at a location 201 that is slightly proximal relative to the distal-most end 511 of the handle 50, but also slightly distal relative to the location 321 at which the working channel 30 splits into two channels. In this embodiment, while the endoscope shaft 20 terminates at this location, it can be seen in FIG. 3 that several components that are incorporated into the endoscope shaft 20 continue to extend proximally beyond this location. Specifically, it can be seen in FIG. 3 that a camera electrical cable 301, that is embedded in, or otherwise disposed within, the wall of the endoscope shaft 20 extends proximally beyond this location towards the electronic control device 54 that is located at a more proximal location within the handle 50 (it should be noted that only a partial view of the camera electrical cable 301 is shown in FIG. 3). The camera electrical cable 301 extends longitudinally along the length of the endoscope shaft 20 so as to be parallel to the working channel 30 that is also running longitudinally through the endoscope shaft 20.

Several other components that are incorporated into the endoscope shaft 20 also continue to extend proximally beyond the location 201 and the location 321 at which the working channel 30 splits into two channels. Specifically, it can be seen in FIG. 3 that, in this embodiment, four steering wires 302a, 302b, 302c, 302d, that are embedded in, or otherwise disposed within, the wall of the endoscope shaft 20 extend proximally beyond this location towards the shaft steering mechanism 56 that is located at a more proximal location within the handle 50 (it should be noted that only a partial view of the four steering wires 302a, 302b, 302c, 302d are shown in FIG. 3). The four steering wires 302a, 302b, 302c, 302d extend longitudinally along the length of the endoscope shaft 20 so as to be parallel to the working channel 30 that is also running longitudinally through the endoscope shaft 20.

Of course, it should be recognized that the endoscope shaft 20 may, in alternative embodiments, have more than one electrical cable extending longitudinally therethrough, depending on the arrangement and functionality of the illumination source and the camera componentry located at the distal end thereof. Likewise, it should be recognized that, in the embodiment shown having four steering wires extending longitudinally therethrough, these four steering wires may be circumferentially arranged within the shaft 20, and/or may be circumferentially attached to the steering collar 309, at different circumferential positions than described hereinabove, depending on the steering directions needed for a given device. Still further, it should be recognized that the endoscope shaft 20 may, in still further embodiments, have more or less than four steering wires extending longitudinally therethrough, depending on the steering capability needed for a given device.

There are a variety of different manufacturing techniques that may be employed so as to embed the camera electrical cable 301 and the steering wires 302a, 302b, 302c, 302d, within the wall structure of the endoscope shaft 20, e.g., extrusion, precision molding, etc. However, these manufacturing techniques may result in the wall structure of the endoscope shaft 20 being relatively bulky or thick. As a result, the outer diameter of the endoscope shaft 20 may be undesirably large, increasing the likelihood that a patient may experience physical discomfort due to a large-diameter endoscope being inserted into the nose, through the sinus cavities and down into the esophagus. Also, in order to keep the outer diameter of the endoscope shaft smaller, the thick or bulky wall structures may force the inner diameter of the working channel to be made undesirably smaller, thereby making it more difficult for instruments to be inserted into and through the working channel. Thus, traditional manufacturing techniques for the endoscope shaft may prevent the resulting endoscopes from being suitable candidates for certain procedures, e.g., unsedated/sedation-free pediatric trans-nasal endoscopy procedures. An example shaft configuration that addresses these challenges, and a method of manufacturing same, is shown and described more fully in Applicant's co-pending U.S. patent application Ser. No. 18/108,562 filed on Feb. 10, 2023, the disclosure of which is hereby incorporated by reference herein in its entirety. In that application, there are described various different weaving patterns for creating the shaft such that some filaments are woven over and some filaments are woven under each of the electrical cable and/or the steering wires, thereby improving the stability of the endoscope shaft 20 while simultaneously minimizing the wall thickness of the endoscope shaft 20, and thereby minimizing the outer diameter of the endoscope shaft 20. Of course, as noted therein, it should be recognized that weaving patterns other than those described therein may be employed, and the filaments employed to create the braided structure of the endoscope shaft 20 may be woven in a different arrangement or order than described therein.

Figure 4:
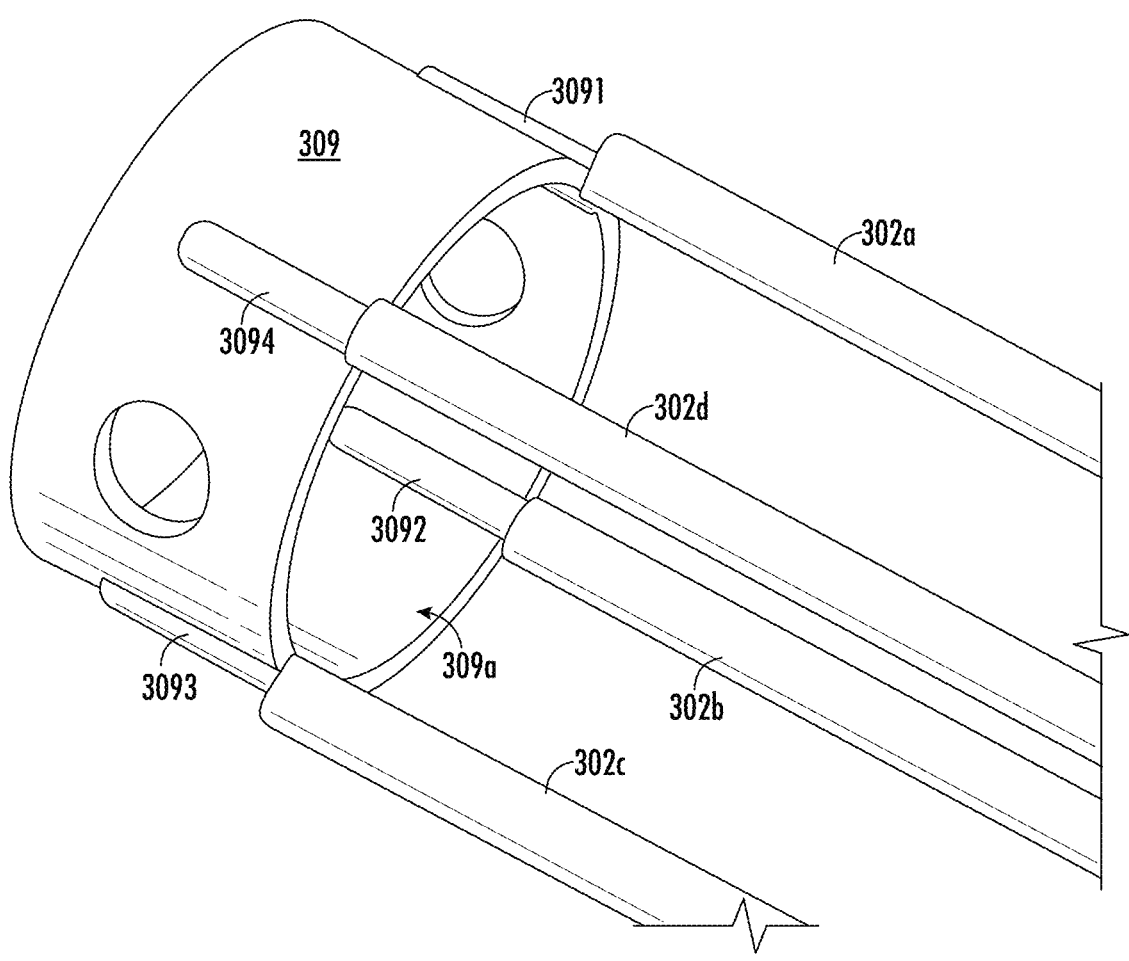
FIG. 4 is rear perspective view of a steering collar at a distal end of the shaft, in accordance with various embodiments.

As set forth above, the handle 50 may include a shaft steering mechanism 56 to control the lateral displacement at the distal end 40 of the endoscope shaft 20. In the embodiment shown in FIG. 3, the handle 50 includes four steering wires 302a, 302b, 302c, 302d disposed within the wall of the endoscope shaft 20 and positioned 90 degrees apart relative to each other. FIG. 4 illustrates an example embodiment of a steering collar 309. The steering collar 309 may be configured with, e.g., a ring-like structure. The steering collar 309 may be embedded within the wall of the endoscope shaft 20, e.g., it may be enclosed in the wall of the endoscope shaft 20 by having the braiding filaments woven therearound or by being molded into a distal component of the shaft.

The steering collar 309 has an interior opening 309a through which the working channel 30 passes. In addition, the steering collar 309 may have various connection points at which the various steering wires are connected. For example, in the embodiment shown, the steering collar 309 has a first connection point 3091 for the first steering wire 302a. The first connection point 3091 is located at, e.g., a 45 degree clockwise position relative to the top-most position along the outer circumference of the working channel 30. Thus, the first connection point 3091 may be advantageously located at a circumferential position relative to the working channel 30 that is the same as the circumferential position of the first steering wire 302a as it extends along the full length of the endoscope shaft 20.

In the embodiment shown, the steering collar 309 also has second, third, and fourth connection points 3092, 3093, and 3094 for connecting the steering collar 309 to the second, third and fourth steering wires 302b, 302c and 302d, respectively. The second, third, and fourth connection points 3092, 3093, and 3094 may be located at, e.g., 135, 225 and 315 degree clockwise circumferential positions, respectively, relative to the top-most position along the outer circumference of the working channel 30. Thus, the second, third, and fourth connection points 3092, 3093, and 3094 may advantageously also be located at respective circumferential positions relative to the working channel 30 that are the same as the respective circumferential positions of the second, third and fourth steering wires 302b, 302c, 302d as they extend along the full length of the endoscope shaft 20.

Figure 5:
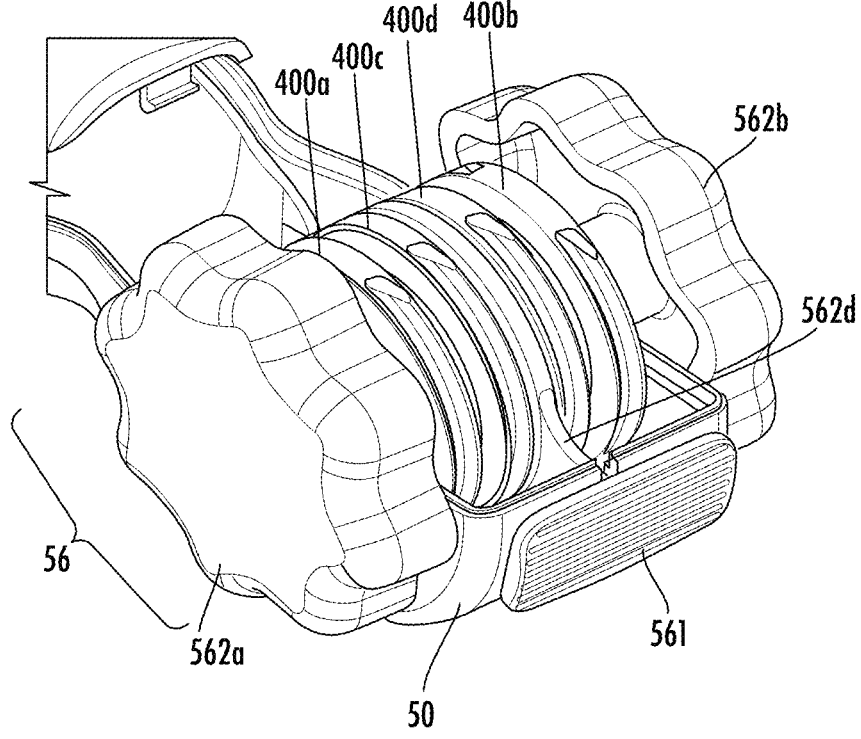
FIG. 5 is a rear perspective view having portions of the handle hidden so as to show some components of a steering mechanism, in accordance with various embodiments.

Referring now to FIG. 5, there is shown a rear perspective, partially cut-away view of the handle 50. The opposite ends of the steering wires 302a, 302b, 302c, 302d (not shown in this view) pass through the handle 50 and are connected to the shaft steering mechanism 56. Specifically, in the embodiment described hereinabove, the opposite, e.g., proximal, ends of the steering wires 302a, 302b, 302c, 302d pass through the distal end of the handle 50 and are connected to steering structures located within the proximal end of the handle 50. Each of the internal steering structures are connected to one or more of the first knob 561 and/or the opposing roller knobs 562a, 562b, which enable a user to actuate the internal steering structures and thereby move, e.g., pull, the steering wires 302a, 302b, 302c, 302d for controlling movements of the distal end 40 of the endoscope shaft 20.

Although shown in FIG. 5 as having a relatively smooth, undulating outer surfaces, the opposing roller knobs 562a, 562b may additionally or alternatively have outer surfaces that have features that provide improved grip thereon. For example, the outer surfaces of the opposing roller knobs 562a, 562b may include, in certain embodiments, one or more grooves and/or ribs formed on the undulations so as to provide additional gripping purchase when operated by the hand of a user.

Figure 6A:
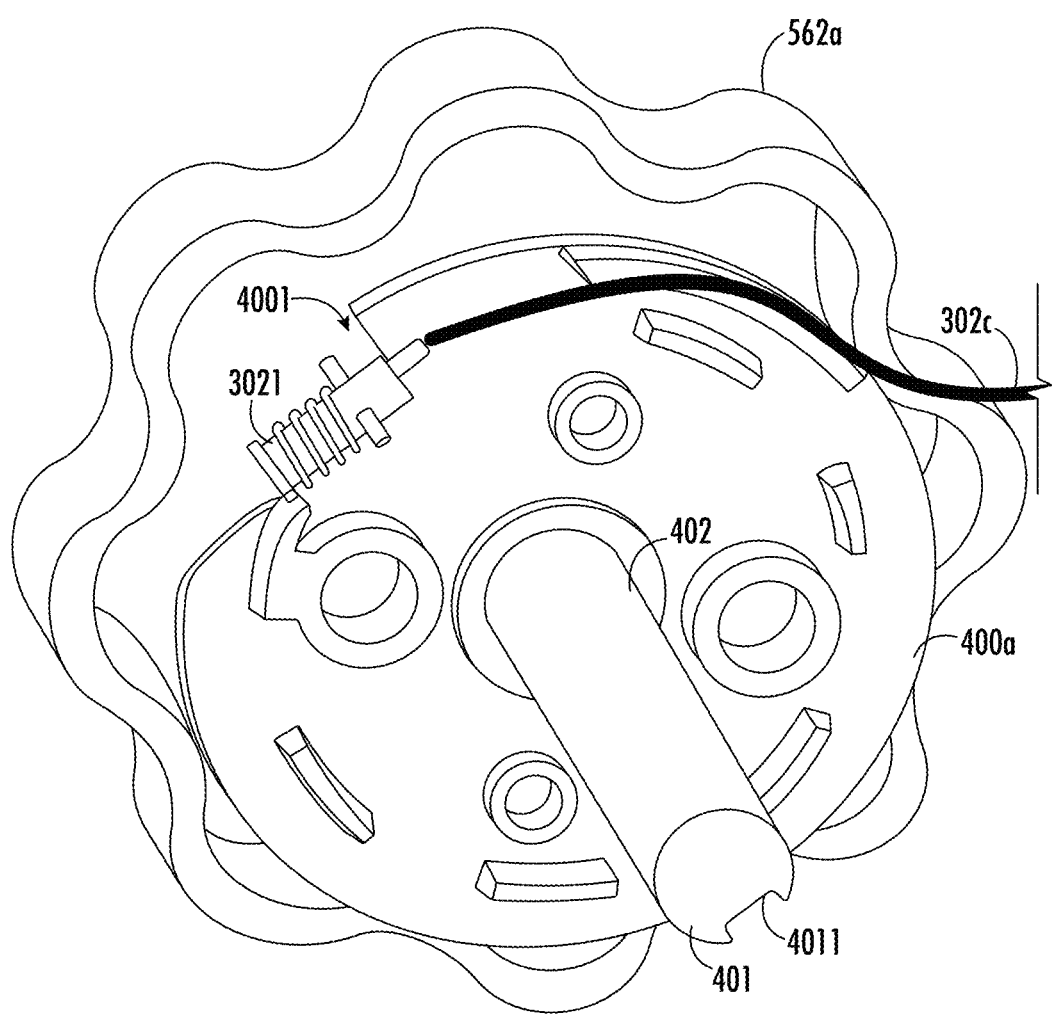
FIGS. 6A and 6B illustrate steering structures that may enable left and right movement of the distal end of the endoscope shaft, in accordance with various embodiments.
Figure 6B:
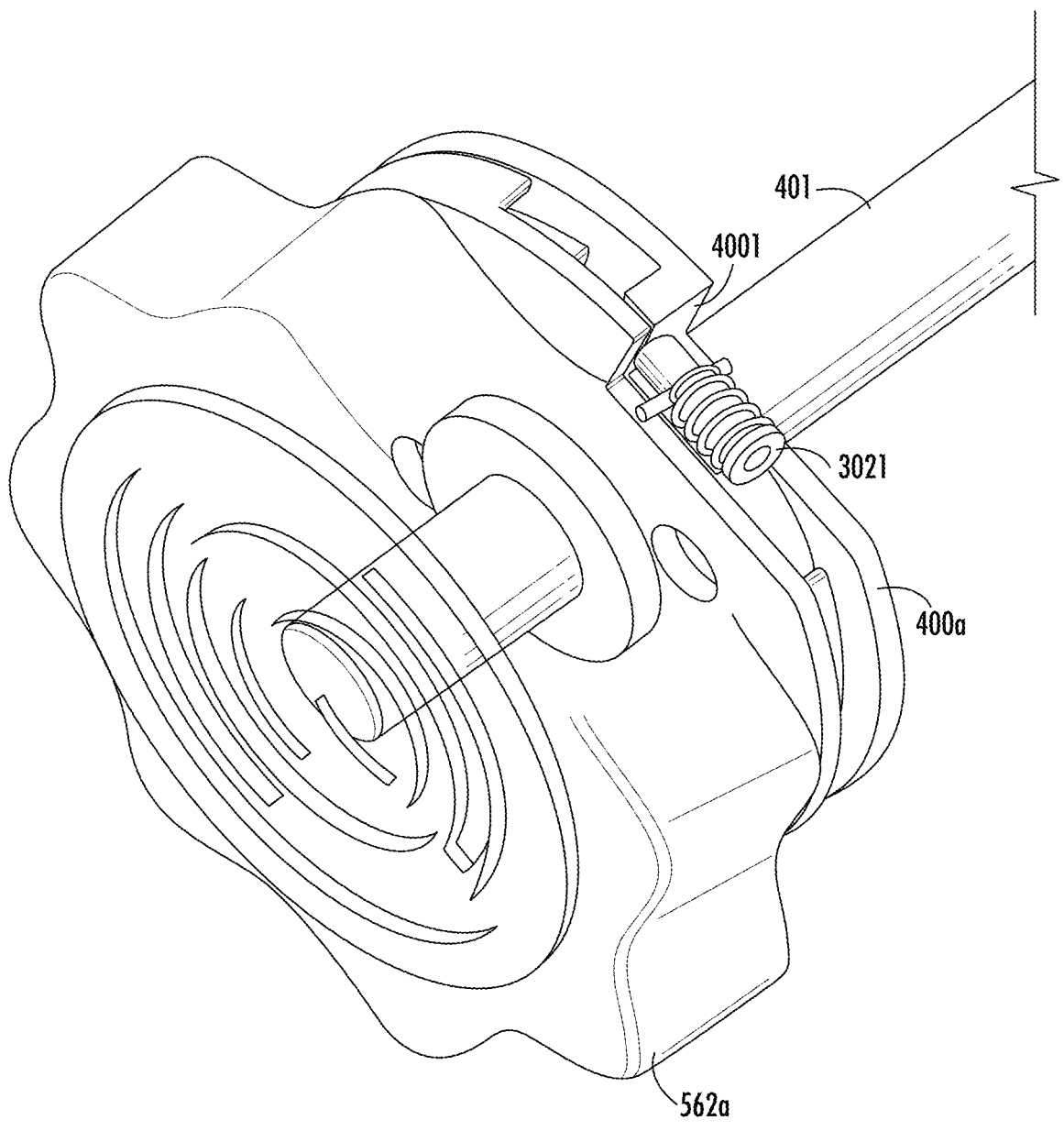

FIGS. 6A and 6B are partial perspective views (with most of the handle 50 and associated structures hidden so as not to obscure the view of various steering structures) that illustrate some additional details of the example embodiment of an internal steering structure. FIG. 6A is a perspective view from one side of the handle 50, while FIG. 6B is a perspective view from the opposite side of the handle 50. Referring to FIGS. 5 and 6A, there is shown a first internal steering structure in the form of a first roller wheel 400a. The first roller wheel 400a resides within the interior of the handle 50 and is generally adjacent to the inside surface of the wall of the handle 50 (the wall of the handle 50 being partially hidden in FIG. 5 and fully hidden in the view of FIG. 6A). FIGS. 5 and 6A also show a first roller knob 562a. The first roller knob 562a resides outside of the wall of the handle 50 and is generally adjacent to the outside surface of the side wall of the handle 50.

The shaft steering mechanism 56 of the trans-nasal endoscope 10, according to various embodiments, may also include a second set of steering structures. In the trans-nasal endoscope 10 shown and described hereinabove, the second set of steering structures may be mirror images of the first roller wheel 400a and the first roller knob 562a. Specifically, the shaft steering mechanism 56 may include a second roller wheel 440b which is located on the opposite side of the handle 50 as compared to the first roller wheel 400a, the second roller wheel also residing within the interior of the handle 50 and being generally adjacent to the inside surface of the opposite wall of the handle 50. In addition, the shaft steering mechanism 56 may also include a second roller knob 562b which is located on the opposite side of the handle relative to the first roller knob 562a, the second roller knob also residing outside of the handle 50 and being generally adjacent to the outside surface of the opposite wall of the handle 50.

It should be understood that, because the first and second steering structures, in the embodiment shown herein, are mirror images of each other, the features of the first steering structure may have symmetrical features in the second steering structure. Having the first and second steering structures be symmetrical, e.g., and on opposite sides of the handle 50 relative to each other, may enable ambidextrous operation of these steering structures. Furthermore, because the first and second steering structures are mirror images of each other, the operation of the first steering structure may result in simultaneous and symmetrical operation of the second steering structure, and vice versa. Thus, for the purposes of illustration, the features and operation of the first steering structures, e.g., the first roller wheel 400a and the first roller knob 562a, will be described below, recognizing that such features and operations may result in similar operation of the second steering structures, e.g., the second roller wheel 400b and the second roller knob 562b.

Referring to FIGS. 6A and 6B, the roller wheel 400a defines an opening 402a at its center. A shaft 401 resides within the opening 402a of the roller wheel 400a. The shaft 401 extends laterally through both sides of the handle 50 (not shown in this view), such that a first end of the shaft 401 is connected to the first roller knob 562a as shown in FIG. 6A, while the second end of the shaft 401 is connected to the second roller knob 562b (shown in FIG. 5). In this particular embodiment, the shaft 401 has a key feature 4011 which mates with corresponding key features (not shown) on the first roller wheel 400a and the first roller knob 562a (likewise, though not shown in this view, the key feature 4011 of the shaft 401 may also mate with corresponding key features on the second roller wheel 400b and the second roller knob 562b). In this way, rotation by a user of the first roller knob 562a causes the shaft 401 to rotate, which thereby also causes the first roller wheel 400a, the second roller wheel 400b and the second roller knob 562b to also rotate. Likewise, because they are all keyed to the shaft 401, rotation by a user of the second roller knob 562b also causes the second roller wheel 400b, the first roller wheel 400a and the first roller knob 562a to also rotate. Alternative embodiments, which are described in greater detail below, may employ additional rotational and lateral mating features, in addition to a keyed shaft, to cause coordinated rotation of the second roller knob 562b, the second roller wheel 400b, the first roller wheel 400a and the first roller knob 562a.

In the embodiment shown, each of the first and second roller wheels has a respective steering wire attached thereto. For example, as shown in FIG. 6A, the first roller wheel 400a is connected to the proximal end of the third steering wire 302c. More specifically, the proximal end of the third steering wire 302c has a crimp 3021 which fixedly attaches it into a slot 4001 on the outer circumference of the first roller wheel 400a. Thus, rotation by a user of the first roller knob 562a causes rotation of the first roller wheel 400a, which in turn causes the proximal end of the third steering wire 302c to be pulled. Pulling the proximal end of the third steering wire 302c causes the length of the third steering wire 302c to move proximally within the shaft wall and thereby cause the steering collar 309 to move proximally at the circumferential position at which the third steering wire 302c is connected. In the embodiment shown, this proximal movement of the third steering wire 302c pulls the left side of the steering collar 309 such that the distal end 44 of the endoscope shaft 20 is steered towards the left.

As set forth above, the second set of steering structures, e.g., the second roller knob 562b and the second roller wheel 400b may be mirror images of the first roller wheel 400a and the first roller knob 562a. Thus, although hidden from view in FIG. 6A, the second roller wheel 400b may be connected to the proximal end of its own corresponding steering wire, e.g., the first steering wire 302a. More specifically, the proximal end of the first steering wire 302a may have a similar crimp which fixedly attaches it into a slot on the outer circumference of the second roller wheel 400b. In this way, rotation by a user of the second roller knob 562b causes rotation of the second roller wheel 400b, which in turn causes the proximal end of the first steering wire 302a to be pulled. Pulling the proximal end of the first steering wire 302a causes the length of the first steering wire 302a to move proximally within the shaft wall and thereby cause the steering collar 309 to move proximally at the circumferential position at which the first steering wire 302a is connected. In the embodiment shown, this proximal movement of the first steering wire 302a pulls the right side of the steering collar 309 such that the distal end 44 of the endoscope shaft 20 is steered towards the right.

Figure 7:
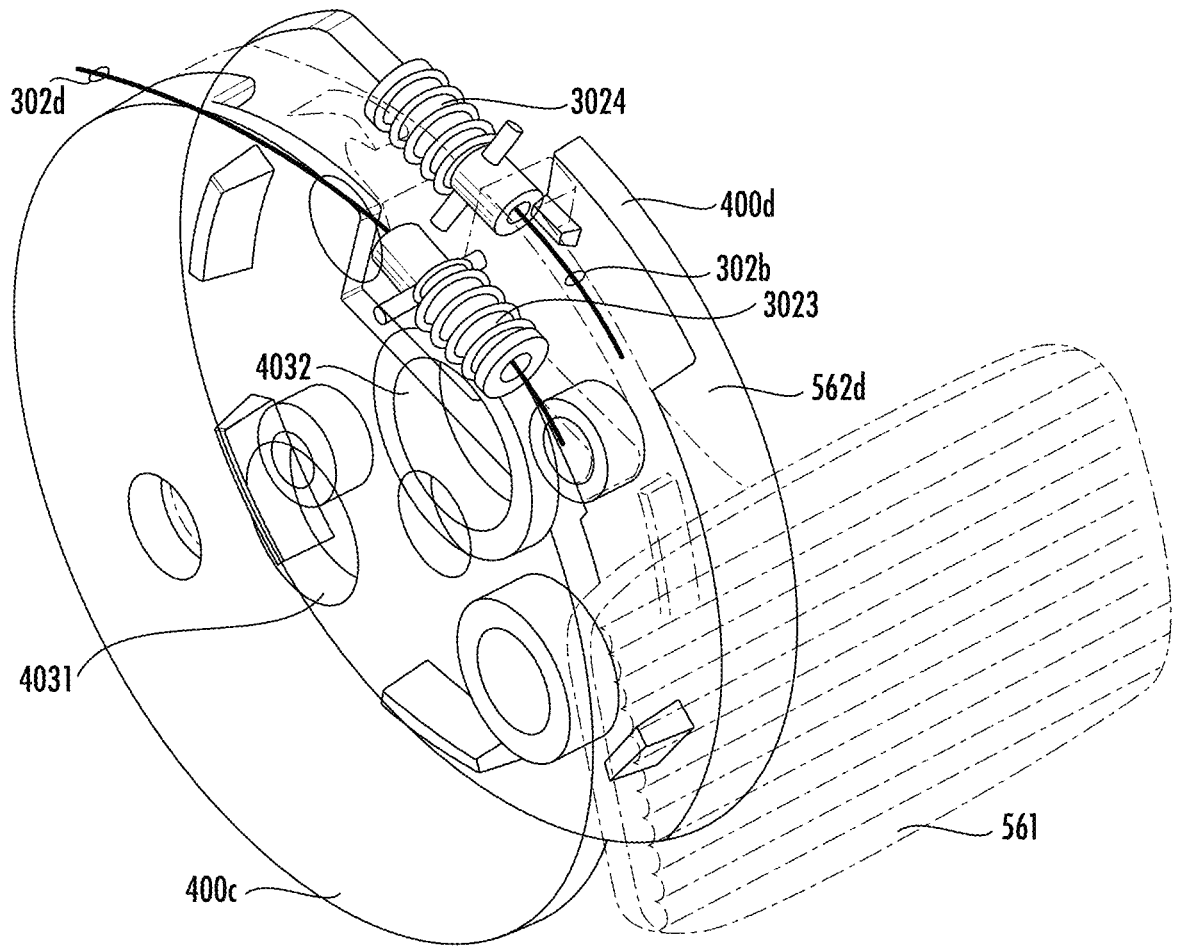
FIG. 7 illustrates steering structures that may enable up and down movement of the distal end of the endoscope shaft, in accordance with various embodiments.

In addition to the shaft steering mechanism 56 including steering structures that enable left and right movement of the distal end 44 of the endoscope shaft 20, the shaft steering mechanism 56 may also include, according to various embodiments, steering structures that enable up and down movement of the distal end 44 of the endoscope shaft 20. FIGS. 5 and 7 illustrate additional steering structures that enable up and down movement of the distal end 44 of the endoscope shaft 20, e.g., FIG. 7 is partial perspective view (with most of the handle 50 and associated structures hidden so as not to obscure the views of these steering structures) that illustrates an example embodiment of such additional internal steering structures. FIGS. 5 and 7 show a third roller wheel 400c and a fourth roller wheel 400d. The third and fourth roller wheels 400c, 400d reside within the interior of the handle 50 and between the first and second roller wheels 400a, 400b. The third roller wheel 400c is generally adjacent to the first roller wheel 400a, while the fourth roller wheel 400d is generally adjacent to the second roller wheel 400b. FIGS. 5 and 7 also show a thumb knob 561. The thumb knob 561 resides outside of the handle 50 and is generally adjacent to the outside surface of the proximal wall of the handle 50.

As shown in FIG. 7, each of the third and fourth roller wheels 400c, 400d define openings 4031, 4032, respectively, at their center. The shaft 401 (shown in FIGS. 6A and 6B) resides within the openings 4031, 4032 of the third and fourth roller wheels 400c, 400d. The thumb knob 561 may have a connector 561 that extends through the proximal wall of the handle 50 so as to connect the thumb knob 561 to the third and fourth roller wheels 400c, 400d. In this way, rotation by a user of the thumb knob 561 causes the third and fourth roller wheel 400c, 400d to rotate about the shaft 401.

In the embodiment shown, each of the third and fourth roller wheels 400c, 400d has a respective steering wire attached thereto. For example, as shown in FIG. 7, the third roller wheel 400c is connected to the proximal end of the fourth steering wire 302d (only a portion of which is shown in FIG. 7). More specifically, the proximal end of the fourth steering wire 302d has a crimp 3023 which fixedly attaches it into a slot on the outer circumference of the third roller wheel 400c. In addition, in the embodiment shown, the fourth steering wire 302d is wound around the top (in this view) of the third roller wheel 400c. Thus, rotation by a user of the thumb knob 561 in a downward direction (in this view) causes clockwise rotation (in this view) of the third and fourth roller wheels 400c, 400d, which in turn causes the proximal end of the fourth steering wire 302d to be pulled in the proximal direction. Pulling the proximal end of the fourth steering wire 302d in the proximal direction causes the length of the fourth steering wire 302d to move proximally within the shaft wall and thereby cause the steering collar 309 to move proximally at the circumferential position at which the fourth steering wire 302d is connected. In the embodiment shown, this proximal movement of the fourth steering wire 302d pulls the top of the steering collar 309 such that the distal end 44 of the endoscope shaft 20 is steered upwardly.

As also shown in FIG. 7, the fourth roller wheel 400d is connected to the proximal end of the second steering wire 302b (only a portion of which is shown in FIG. 7). More specifically, the proximal end of the second steering wire 302b has a crimp 3024 which fixedly attaches it into a slot on the outer circumference of the fourth roller wheel 400d. In addition, in the embodiment shown, the second steering wire 302b is wound around the bottom (in this view) of the fourth roller wheel 400d. Thus, rotation by a user of the thumb knob 561 in an upward direction (in this view) causes counter-clockwise rotation (in this view) of the third and fourth roller wheels 400c, 400d, which in turn causes the proximal end of the second steering wire 302b to be pulled in the proximal direction. Pulling the proximal end of the second steering wire 302b in the proximal direction causes the length of the second steering wire 302b to move proximally within the shaft wall and thereby cause the steering collar 309 to move proximally at the circumferential position at which the second steering wire 302b is connected. In the embodiment shown, this proximal movement of the second steering wire 302b pulls the bottom of the steering collar 309 such that the distal end 44 of the endoscope shaft 20 is steered downwardly.

Of course, the above-described arrangement of the steering mechanism 56 is merely one possible such arrangement, and other mechanisms for effectuating the steering of the distal end 44 of the endoscope shaft 20 are also contemplated. For example, steering structures other than, e.g., the above-described roller wheels and roller knobs, may be employed to actuate the left and right movement of the distal end 44 of the endoscope shaft 20. Likewise, steering structures other than, e.g., the above-described roller wheels and thumb knob, may be employed to actuate the up and down movement of the distal end 44 of the endoscope shaft 20. Furthermore, there may be less than or more than the four steering wires illustrated in the embodiment described hereinabove, depending on the number of different directions of movements desired for the distal end 44 of the endoscope shaft 20. Still further, the steering wires may be connected in different circumferential locations around the steering collar 309 such that the steering mechanisms employed in the handle 50 use the steering wires to pull the steering collar 309 in different directions.

As set forth above, various embodiments may employ features other than a keyed shaft to cause coordinated rotation of the second roller knob 562b, the second roller wheel 400b, the first roller wheel 400a and the first roller knob 562a. Additionally or alternatively, various embodiments may enable the tension in the steering control mechanism, e.g., the tension in the steering wires, to be optimized prior to being used in a surgical procedure, e.g., to be optimized during a manufacturing process or the like. Traditionally, steering mechanisms such as steering wires are difficult to adequately and/or accurately tension during manufacturing, resulting in less than optimal steering capabilities.

Figure 8:
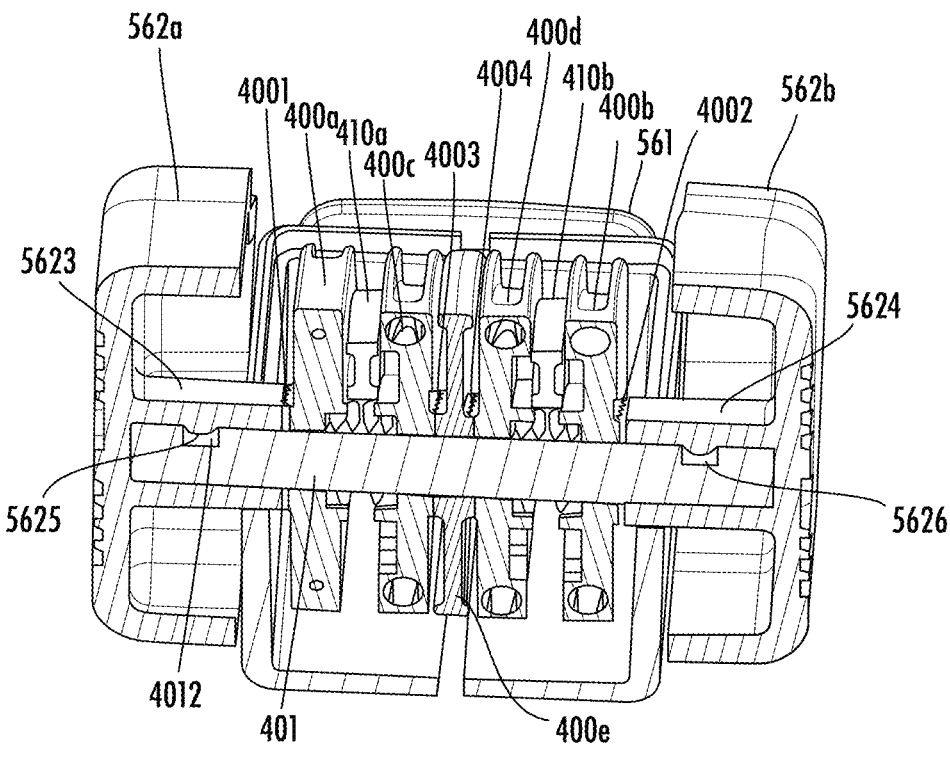
FIG. 8 is a rear cross-sectional view of the handle that illustrates additional details of a steering mechanism, in accordance with various embodiments.
Figure 9:
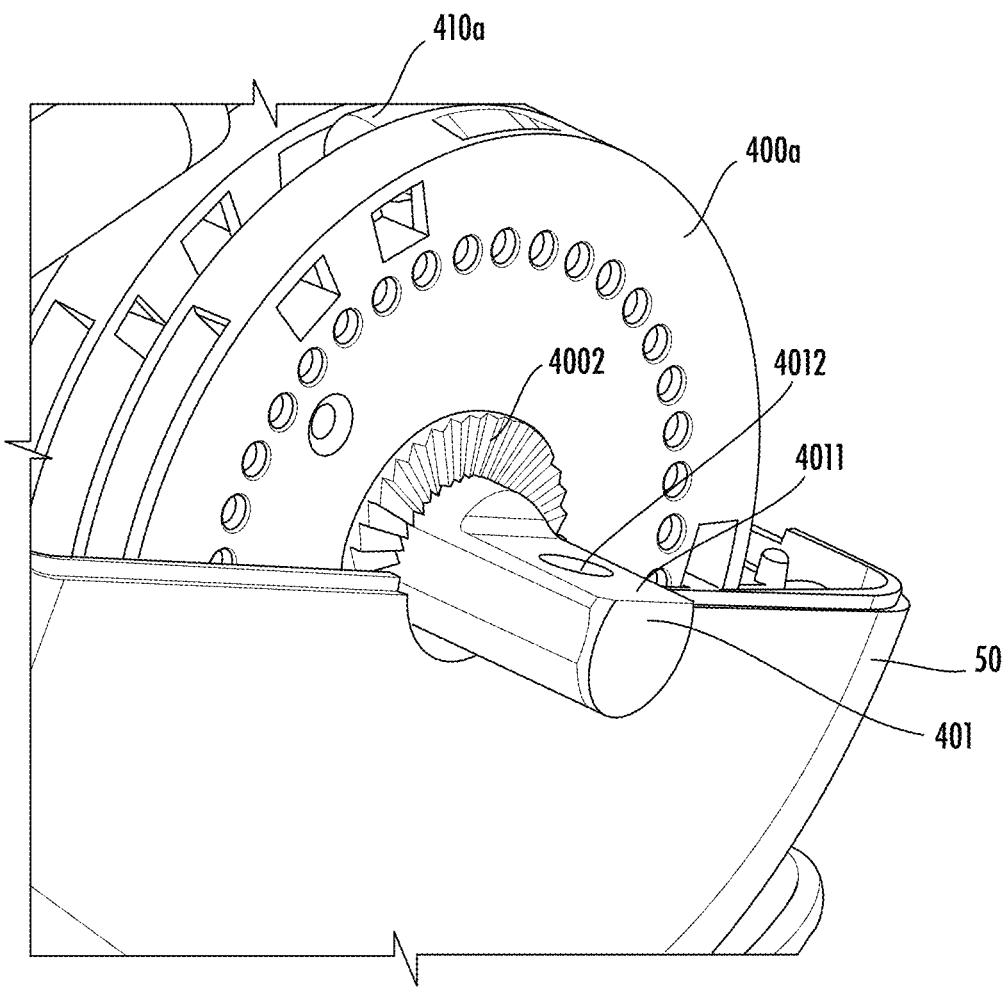
FIG. 9 is a side perspective view with portions of the handle hidden so as to illustrate additional details of the steering mechanism, in accordance with various embodiments.

FIG. 8 is a front view of the handle 50 with most of the features thereof being cut-away so as to allow a cross-sectional view of certain components of a steering mechanism. FIG. 8 illustrates that first and second roller wheels 400a, 400b have, on their outer side walls, a set of ratcheting teeth 4001, 4002, respectively (FIG. 9 is a side perspective view having part of the handle 50 being hidden so as to better illustrate the ratcheting teeth 4001 located on the outer side wall of the first roller wheel 400a). The sets of ratcheting teeth 4001, 4002 provide a tensioning feature that enables the first and second roller wheels 400a, 400b to generate a resting tension force on the steering wire prior to the first and second roller wheels 400a, 400b being actuated during a surgical procedure. In other words, during a manufacturing process or the like, the resting tension of the steering wires, e.g., the tension in the steering wires before they are actuated by a user during a surgical procedure, can be established such that they are pre-set at an optimal amount of tension. Advantageously, these same first and second roller wheels 400a, 400b may be subsequently actuatable by a user, e.g., by the user turning the first and/or second roller knobs 562a, 562b, during the surgical procedure to generate the above-described steering tension forces on the steering wires so as to steer the distal region of the shaft 20 during the surgical procedure.

As shown in FIGS. 8 and 9, the sets of ratchet teeth 4001, 4002 may be configured so as to enable the first and second roller wheels 400a, 400b to be rotated relative to the handle 50 in a first rotational direction, e.g., clockwise, but to prevent rotation of the first and second roller wheels 400a, 400b relative to the handle 50 in the opposite rotational direction, e.g., counter-clockwise (or vice versa). In this way, the sets of ratchet teeth 4001, 4002 may be configured so as to maintain the resting tension force on the steering wire(s) prior to the first and/or second roller wheels 400a, 400b being actuated. In embodiments, and as described hereinabove, the first and/or second roller wheels 400a, 400b may be actuatable by the user during a surgical procedure to generate steering tension forces in opposite longitudinal directions on their respective steering wires so as to control steering of the distal region 40 of the shaft 20 in the left and right directions.

Having the respective sets of ratcheting teeth 4001, 4002 be disposed on the outer sidewalls of the third and fourth roller wheels 400c, 400d enables the sets of ratcheting teeth 4001, 4002 to engage matching sets of ratcheting teeth on, e.g., inwardly-extending edges of the first and second roller knobs 562a, 562b. In this way, actuation by a user during a surgical procedure of the first and second roller knobs 562a, 562b causes engagement of these respective ratcheting teeth and thereby rotation of the first and second roller wheels 400a, 400b.

In still further embodiments, the third and fourth roller wheels 400c, 400d may also include tensioning features as described hereinabove. For example, as shown in FIG. 8, the third and fourth roller wheels 400c, 400d may also include respective sets of ratcheting teeth 4003, 4004. The third and fourth roller wheels 400c, 400d including respective sets of ratcheting teeth 4003, 4004 enables the third and fourth roller wheels 400c, 400d to be rotated relative to the handle 50 in a first rotational direction, e.g., clockwise, but to prevent rotation of the third and fourth roller wheels 400c, 400d relative to the handle 50 in the opposite rotational direction, e.g., counter-clockwise (or vice versa). In the embodiment shown, the respective sets of ratcheting teeth 4003, 4004 are disposed on the inner sidewalls of the third and fourth roller wheels 400c, 400d, although other locations are contemplated. Having the respective sets of ratcheting teeth 4003, 4004 be disposed on the inner sidewalls of the third and fourth roller wheels 400c, 400d enables the sets of ratcheting teeth 4003, 4004 to engage matching sets of ratcheting teeth on the outer side walls of the support structure 400e of the thumb knob 561, so that actuation by a user during a surgical procedure of the thumb knob 561 causes engagement of the respective ratcheting teeth and thereby rotation of the third and fourth roller wheels 400c, 400d. As set forth above, the third and fourth roller wheels 400c, 400d are also actuatable by the user during a surgical procedure to generate steering tension forces in opposite longitudinal directions on their respective steering wires so as to control steering of the distal region 40 of the shaft 20 in the up and down directions.

Additionally, there may be instances when, e.g., during a manufacturing process, the pre-set tension on the steering wires needs to be adjusted. For example, there may be instances when, e.g., during a manufacturing process, the steering wires are caused to be too tight and are desired to be loosened, or may be caused to be too loose and are desired to be further tightened. Various other reasons are contemplated why such pre-tensioned steering wires may need to be further adjusted, e.g., temperature changes, generally loosening or settling of components, etc.

In embodiments, in addition to the actuation mechanisms (e.g., the roller wheels) being configured to generate and maintain a resting tension on the steering wire prior to the first actuation mechanism being actuated during the surgical procedure, the steering control mechanism may also include a resting tension adjustment feature. This resting tension adjustment feature may enable selective engagement and disengagement of the resting tension feature so as to enable the resting tension force on the steering wire to be adjusted.

Figure 10:
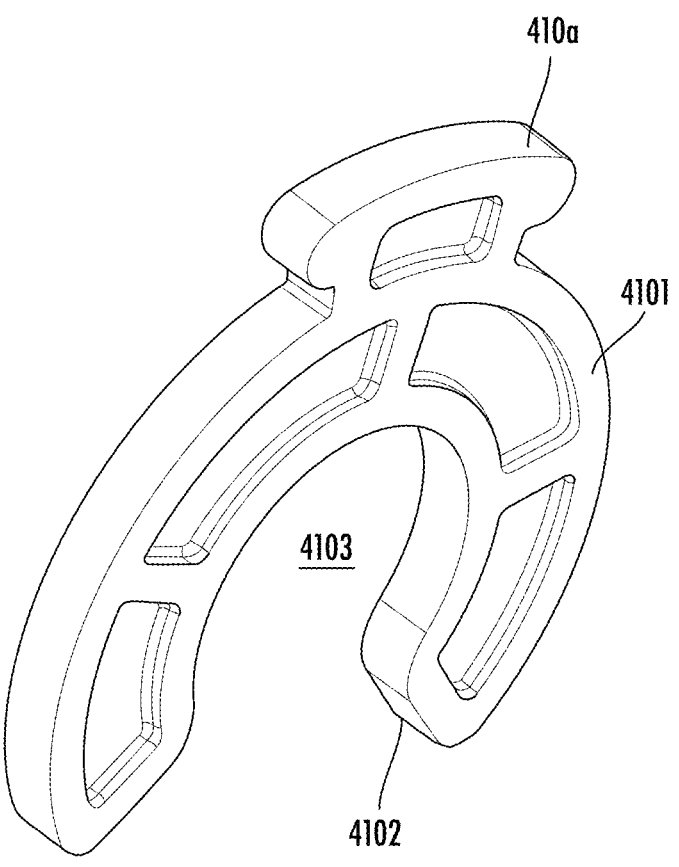
FIG. 10 is a perspective view of a spacer, in accordance with various embodiments.

In certain embodiments, the resting tension adjustment feature includes spacers. For example, FIG. 10 illustrates a spacer 410a, according to embodiments. Spacer 410a may have a body 4101 that is generally circular in shape, having a central opening 4103 through which the shaft 401 may be disposed. The body 4101 of the spacer 410a may have a circumferential opening 4102 along a portion of its circumference that is in communication with the central opening 4103 and that allows the spacer 410a to be removed from the shaft 401 when adjustment of the steering wire tensions are desired.

FIG. 8 illustrates spacers 410a, 410b in position within a steering mechanism. Advantageously, the spacers 410a, 410b can function to selectively maintain the ratchet teeth in relative engagement (e.g., so as to maintain the resting tension on the steering wire prior to an actuation mechanism being actuated during the surgical procedure) and/or to selectively enable the ratchet teeth to be disengaged (e.g., so as to enable the resting tension on the steering wire to be adjusted prior to the actuation mechanism being actuated during the surgical procedure).

In the embodiments described above, the spacer 410a is positionable between the first and third roller wheels 400a, 400c, while the spacer 410b is positionable between the second and fourth roller wheels 400b, 400d. In such an arrangement, the spacer 410a helps to maintain engagement of the ratchet teeth 4001 on the outer side wall of the first roller wheels 400a with the mating ratcheting teeth on the inwardly-disposed edge of the roller knob 562a, while simultaneously helping to maintain engagement of the ratchet teeth 4003 on the inner side wall of the third roller wheel 400c with the mating ratcheting teeth on the outer side wall of the support structure 400e of the thumb knob 561. Likewise, in such an arrangement, the spacer 410b helps to maintain engagement of the ratchet teeth 4002 on the outer side wall of the second roller wheel 400b with the mating ratcheting teeth on the inwardly-disposed edge of the roller knob 562b, while simultaneously helping to maintain engagement of the ratchet teeth 4004 on the inner side wall of the fourth roller wheel 400d with the mating ratcheting teeth on the opposite side wall of the support structure 400e of the thumb knob 561. In this way, when the spacers 410a, 410b are in position, engagement of the ratchet teeth is maintained and thus the resting tension is maintained on the steering wire prior to the first actuation mechanism being actuated during the surgical procedure. Alternatively, when the spacer is not thus positioned, the respective ratchet teeth may be disengageable, so as to enable the resting tension on the steering wire to be adjusted prior to the first actuation mechanism being actuated during the surgical procedure. Once the resting tension on the steering wires is adjusted, the spacers 410a, 410b may be returned to their respective positions so as to maintain the adjusted tension.

It should be recognized that other configurations may be employed for generating the resting tension force on the steering wires prior to the first and second roller wheels 400a, 400b being actuated during a surgical procedure, e.g., during a manufacturing process or the like when the tension in the steering wires is established or pre-set to an optimal amount of tension before the steering wires are actuated by a user during a surgical procedure. For example, while the above-described embodiments employ sets of complementary ratcheting teeth on the roller wheels and roller knobs, e.g., the ratchet teeth 4002 on the outer side wall of the second roller wheel 400b mating with the ratcheting teeth on the inwardly-disposed edge of the roller knob 562b, alternative embodiments may include separate ratchet wheels mounted on respective roller wheels for this purpose.

Figure 15:
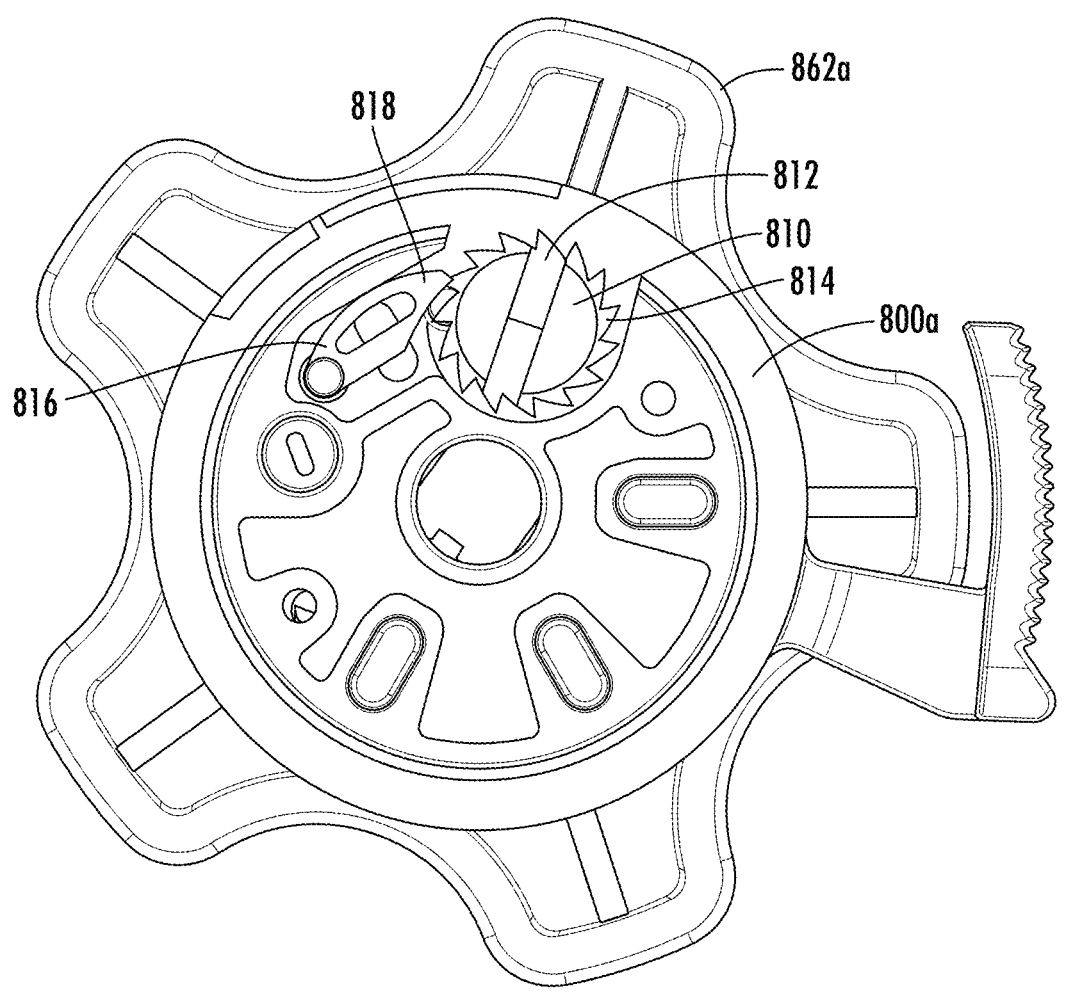
FIG. 15 is a side view of various components maintained with a handle, illustrating a rotatably mounted steering wire resting tension adjustment mechanism, in accordance with various embodiments.

An example of such an arrangement is shown and described in connection with FIG. 15, which is a side view of various components maintained with the handle, with the outer shell of the handle removed from view so as not to obscure these features. FIG. 15 illustrates an exemplary roller wheel, e.g., roller wheel 800a, that is rotatably connected to roller knob 862a via a rotatable shaft 801. Rotatably mounted onto the side of the roller wheel 800b is a ratchet wheel 810. The ratchet wheel 810 has a through-hole 812 through which a steering wire and its end crimp (both of which not shown here) may be fed. The ratchet wheel 810 may also include, around its outer circumferential edge, a set of ratchet teeth 814. Also rotatably mounted onto the side of the roller wheel 800b is a leaf spring 816. As will be evident below, it should be recognized that other types of spring, besides a leaf spring 816 as shown, may also be employed.

During, e.g., a manufacturing process, a steering wire and its end crimp are fed into the through-hole 812 of the ratchet wheel 810. In order to and until an optimal resting tension is achieved for the steering wire, the ratchet wheel 810 may be rotated relative to the roller wheel 800a. In the view shown, the ratchet wheel 810 is rotated clockwise relative to the roller wheel 800a in order to increase the resting tension on the steering wire (not shown) that was fed into the ratchet wheel 810. The leaf spring 816 has a distal finger 818 or the like that engages the ratchet teeth 814 of the ratchet wheel 810. Advantageously, the distal finger 818 and the ratchet teeth 814 are configured such that the distal finger 818 and the ratchet teeth 814 permit rotatable movement of the ratchet wheel 810 relative to the roller wheel 800a in only one direction (in this embodiment and in the view shown, the distal finger 818 and the ratchet teeth 814 are configured such that they permit rotatable movement of the ratchet wheel 810 relative to the roller wheel 800a in only the clockwise direction). Conversely, the distal finger 818 and the ratchet teeth 814 are configured such that the distal finger 818 and the ratchet teeth 814 prevent rotatable movement of the ratchet wheel 810 relative to the roller wheel 800a in the opposite direction (in this embodiment and in the view shown, the distal finger 818 and the ratchet teeth 814 are configured such that they prevent rotatable movement of the ratchet wheel 810 relative to the roller wheel 800a in the counter-clockwise direction). In this way, the ratchet wheel 810 may be rotated clockwise relative to the roller wheel 800a (and the steering wire that was fed into the ratchet wheel 810 may be provided with its resting tension) until an optimal resting tension is achieved for the steering wire, and that optimal resting tension may be maintained by the leaf spring 816 preventing clockwise rotation thereof.

Should the resting tension of the steering wire need to be further adjusted (e.g., due to slippage, temperature changes, shipping, etc.), the ratchet wheel 810 may be further rotated relative to the roller wheel 800a as needed. For example, should the resting tension of the steering wire need to be tightened, the ratchet wheel 810 may simply be further rotated clockwise relative to the roller wheel 800a and the ratchet teeth 814 of the ratchet wheel 810 may simply pass over the distal finger 818 of the leaf spring 816 until the desired resting tension is achieved. Conversely, should the resting tension of the steering wire need to be loosened, the leaf spring 816 may be lifted off of the ratchet teeth 814 of the ratchet wheel 810, whereby the ratchet wheel 810 may then be rotated counter-clockwise relative to the roller wheel 800a as needed until the desired resting tension of the steering wire is achieved, at which point the distal finger 818 of the leaf spring 816 may be released back into engagement with the ratchet teeth 814 of the ratchet wheel 810 to lock the ratchet wheel 810 in place. Advantageously, the roller wheel 800a may be subsequently actuatable by a user, e.g., by the user turning the first and/or second roller knobs 862a during the surgical procedure to generate the above-described steering tension forces on the steering wires so as to steer the distal region of the shaft 20 during the surgical procedure. Of course, the above-described embodiment is employable for use with any of the roller wheels and roller knobs described hereinabove.

As set forth above, in various embodiments, the steering control mechanism 56 may employ additional rotational and lateral mating features, in addition to a keyed shaft, to cause coordinated rotation of the second roller knob 562b, the second roller wheel 400b, the first roller wheel 400a and the first roller knob 562a. For example, referring to FIG. 9, the shaft 401 is shown as having a generally flat cross-sectional region 4011 (e.g., it being generally flat relative to its otherwise generally round cross-sectional profile). This flat region 4011 of the shaft 401 may mate with a similar generally flat region on the inwardly-extending tube portions 5623, 5624 of the first and second roller knobs 562a, 562b, respectively. In this way, each end of the shaft 401 and each of the first and second roller knobs 562a, 56b have corresponding or cooperating rotational mating features that, when the roller knobs are press-fit onto the ends of the shaft

401, ensure that the shaft 401 rotates when the roller knobs 562a, 562b are rotated. Of course, it should be recognized that the rotational mating features, e.g., the respective flat regions on the shaft 401 and on the inwardly-extending tube portions 5623, 5624 of the first and second roller knobs 562a, 562b, may have any conceivable shape that enables the roller knob 562a, 562b and the ends of the shaft 401 to be rotationally mated with each other so as to prevent relative rotational movement therebetween. The description hereinabove of respective flat regions on the shaft 401 and the inwardly-extending tube portions 5623, 5624 of the first and second roller knobs 562a, 562b are merely exemplary.

FIG. 9 also illustrates that shaft 401 may include near to its ends, and advantageously on the flat regions 4011, a void 4012 in the shape of an opening or indentation. The inwardly-extending tube portions 5623, 5624 of the first and second roller knobs 562a, 562b (and advantageously the flat region on these inwardly-extending tube portions 5623, 5624 of the first and second roller knobs 562a, 562b) may each include a protuberance, e.g., in the shape of a bump or any other outwardly-extending shape (see, for example, protuberances 5625, 5626 on the inwardly-extending tube portions 5623, 5624 of the first and second roller knobs 562a, 562b, in FIG. 8). These protuberances may each mate with, e.g., engage with or at least partially enter, the voids 4012 on the ends of the shaft 401 so as to keep the roller knobs 562a, 562b maintained on their respective ends of the shaft 401. In this way, each of the roller knobs 562a, 562b and the shaft 401 have corresponding or cooperating lateral mating features that, when the roller knobs 562a, 562b are press-fit onto the ends of the shaft 401, maintain the roller knobs 562a, 562b on the shaft 401. Of course, it should be recognized that the lateral mating features, e.g., the voids and/or protuberances, may have any conceivable shape that enables the roller knob 562a, 562b and the ends of the shaft 401 to be laterally mated with each other so as to prevent relative lateral movement therebetween. It should also be recognized that, to the extent that the lateral mating features take the form of cooperating voids and/or protuberances, such voids and protuberances may be located on either one of the roller knobs 562a, 562b or the ends of the shaft 401, and that the description hereinabove of the voids 4011 being disposed on the shaft 401 and the protuberances being disposed on the roller knobs 562a, 562b are merely exemplary.

In addition, the voids 4012 on the flat regions 4011 of the shaft 401, and the protuberances on the inwardly-extending tube portions 5623, 5624 of the first and second roller knobs 562a, 562b, are advantageously located in lateral positions relative to each other such that, when the protuberances are mated with the voids, the roller knobs 562a, 562b are engaged with the roller wheels 400a, 400b. More specifically, in embodiments, the voids 4012 are laterally positioned on the flat regions 4011 of the shaft 401, and the protuberances are laterally positioned on the inwardly-extending tube portions 5623, 5624 of the first and second roller knobs 562a, 562b, such that, when the protuberances are mated with the voids 4011, the ratchet teeth on the inwardly-extending tube portions 5623, 5624 of the first and second roller knobs 562a, 562b engage the ratchet teeth on the outer side walls of the roller wheels 400a, 400b, thereby enabling rotation of the roller knobs 562a, 562b to cause rotation of the roller wheels 400a, 400b to effectuate pulling of the steering wires and steering of the distal region 40 of the shaft 20. Of course, in the embodiment shown, the presence of the spacers 410a, 410b also help to keep the ratchet teeth on the inwardly-extending tube portions 5623, 5624 of the first and second roller knobs 562a, 562b engaged with the ratchet teeth on the outer side walls of the roller wheels 400a, 400b during a surgical procedure.

As mentioned above, providing rotational and lateral mating features on the roller knobs 562a, 562b and the shaft 401 enables the roller knobs 562a, 562b to be press-fit onto respective ends of the shaft 401 during assembly. Press-fitting these components during manufacturing may greatly simplify assembly of the handle 50, e.g., thereby saving in material and labor costs, avoiding the use of messy gluing or other connective materials and/or processes for these components, and helping to prevent assembly errors.

In embodiments, in addition to the actuation mechanisms (e.g., the roller wheels) being configured to generate and maintain a steering tension force on the steering wire while the first actuation mechanism is being actuated during the surgical procedure, the steering control mechanism may also include a steering tension braking feature. This steering tension braking feature may enable selective engagement and disengagement by the user so as to brake the steering wire, thereby preventing the shaft from inadvertently or unintentionally moving after a desired steered position has been achieved. More specifically, once a user has steered, e.g., the distal tip of the shaft, to a desired steered position, the user may activate the steering tension braking feature so as to maintain the distal tip of the shaft in the desired steered position such that external forces acting on the shaft, e.g., the forces provided by the friction or pressure between the body and the shaft, do not move the distal tip away from the desired steered position. Additionally or alternatively, the steering tension braking feature may help maintain the distal tip of the shaft in the desired steered position such that internal forces built up within the shaft itself, e.g., the resiliency or spring-back tension created within the structures of the shaft which collectively contribute to the bent shaft structures tending to want to return to their unbent position, do not move the distal tip away from the desired steered position.

Figure 11:
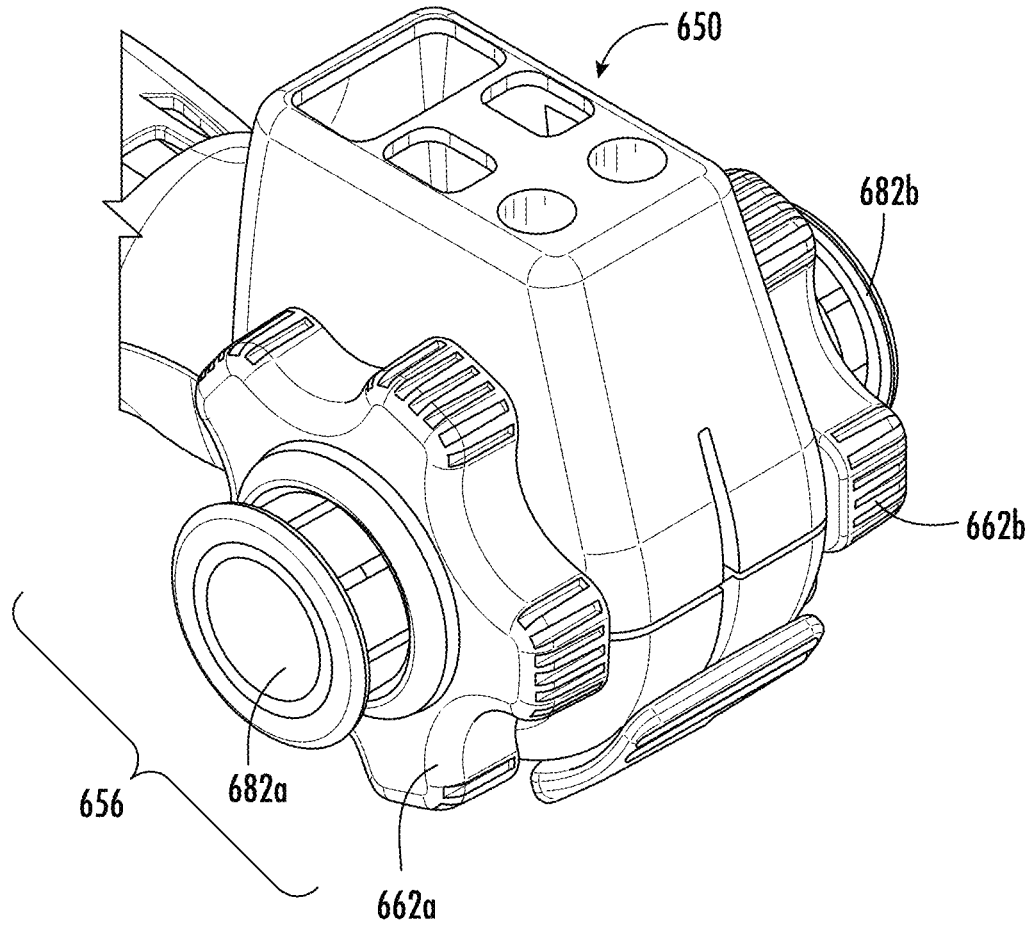
FIG. 11 is a rear view of a handle, with some of the components of the handle removed, illustrating a steering tension braking feature, in accordance with various embodiments.

FIG. 11 illustrates an example of some of the aspects a steering tension braking feature, according to various embodiments. FIG. 11 is a rear view of a handle 650, with some of the components of the handle 650 removed so as to focus on various specific features thereof. FIG. 11 illustrates the shaft steering mechanism 656 including opposing roller knobs 662a, 662b located on the opposite side of the handle 650 for controlling movements of the distal end of the endoscope shaft. Projecting radially outward from the opposing roller knobs 662a, 662b are steering wire braking mechanisms 682a, 682b.

Figure 12:
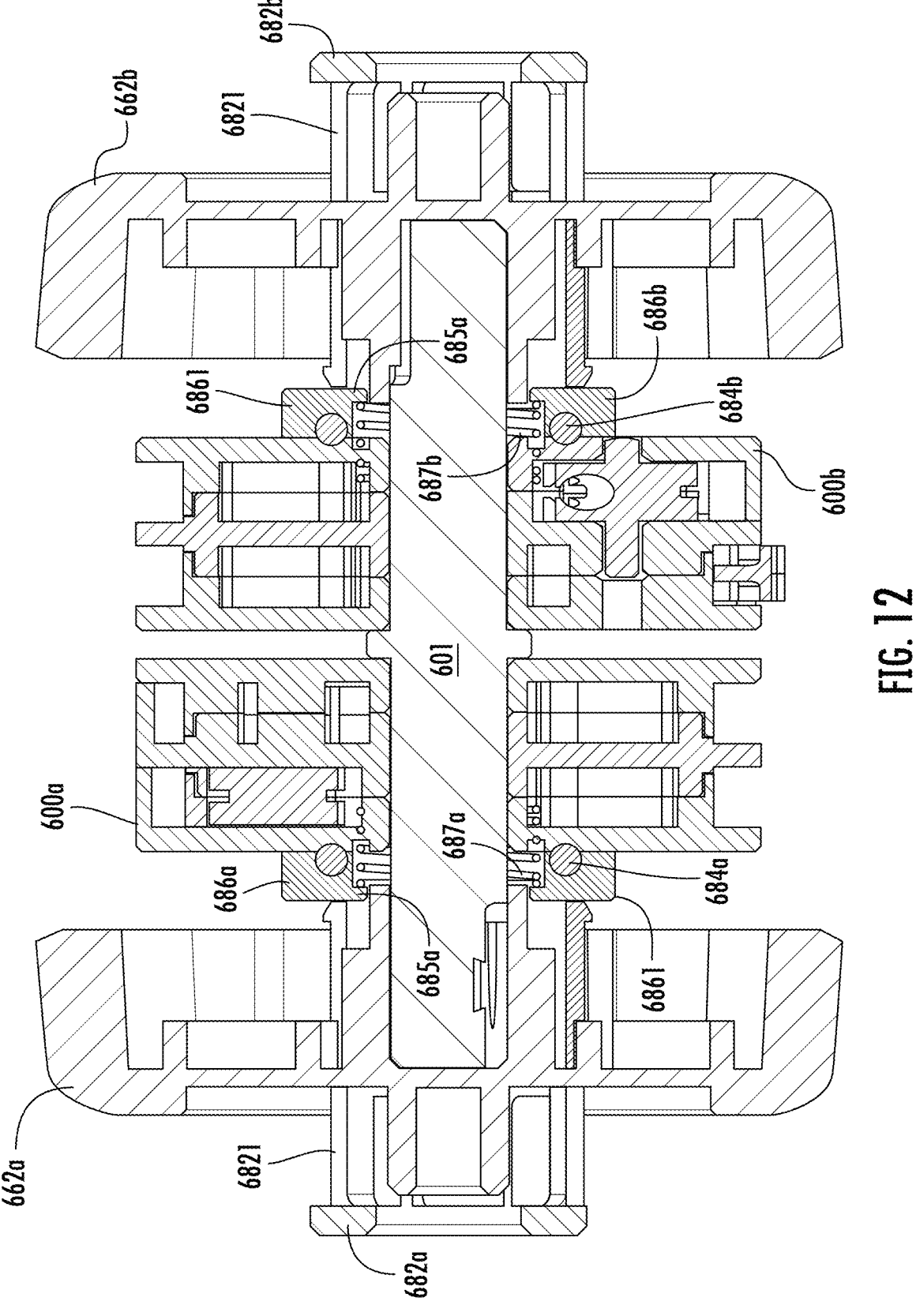
FIG. 12 is a rear cross-sectional view of the steering mechanisms within a handle, with various features removed so as not to obscure specific features thereof, illustrating the steering tension braking feature, in accordance with various embodiments.

FIG. 12 is a rear cross-sectional view of the steering mechanisms within the handle 650, again with various features removed so as not to obscure specific features thereof. As shown in FIG. 12, a shaft 601 resides within the handle 650 and extends laterally through both sides of the handle 650 (not shown in this view), such that a first end of the shaft 601 is connected, e.g., via key arrangement, to the first roller knob 662a, while the second end of the shaft 601 is connected to the second roller knob 662b. Rotation by a user of the first roller knob 662a causes the shaft 601 to rotate, which thereby also causes a first roller wheel 600a, a second roller wheel 600b and the second roller knob 662b to also rotate. Likewise, because they are all keyed to the shaft 601, rotation by a user of the second roller knob 662b also causes the second roller wheel 600b, the first roller wheel 600a and the first roller knob 662a to also rotate. Although not shown in FIG. 12, each of the first and second roller wheels 600a, 600b, has a respective steering wire attached thereto.

Located radially outwardly relative to the first roller wheel 600a and the second roller wheel 600b are o-rings 684a, 684b. The o-rings 684a, 684b are supported by o-ring retention members 686a, 686b, which in this embodiment are formed by respective annular rings (although other shapes are contemplated) having a recess into which the o-rings 684a, 684b may reside. Each of the o-ring retention members 686a, 686b, include an interior annular lip 685a, 685b which supports, and against which is biased, a spring 687a, 687b. A radially outer surface 6861 of each of the o-ring retention members 686a, 686b is engaged by fingers 6821 of a respective one of the steering wire braking mechanisms 682a, 682b.

Figure 13A:
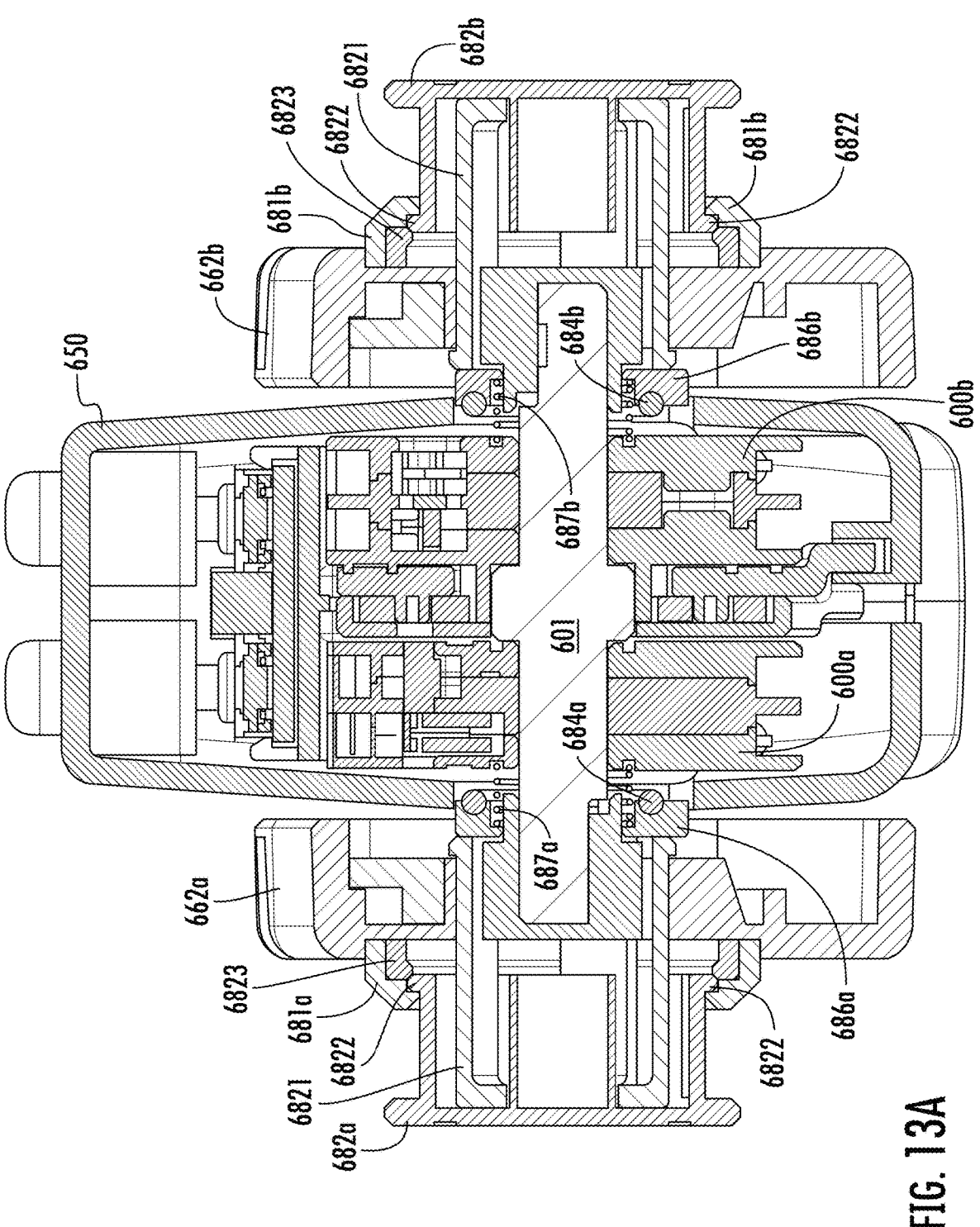
FIG. 13A through 13D are rear cross-sectional views of a handle showing additional features thereof, and showing steering wire braking mechanisms respectively disengaged and engaged, in accordance with various embodiments.
Figure 13B:
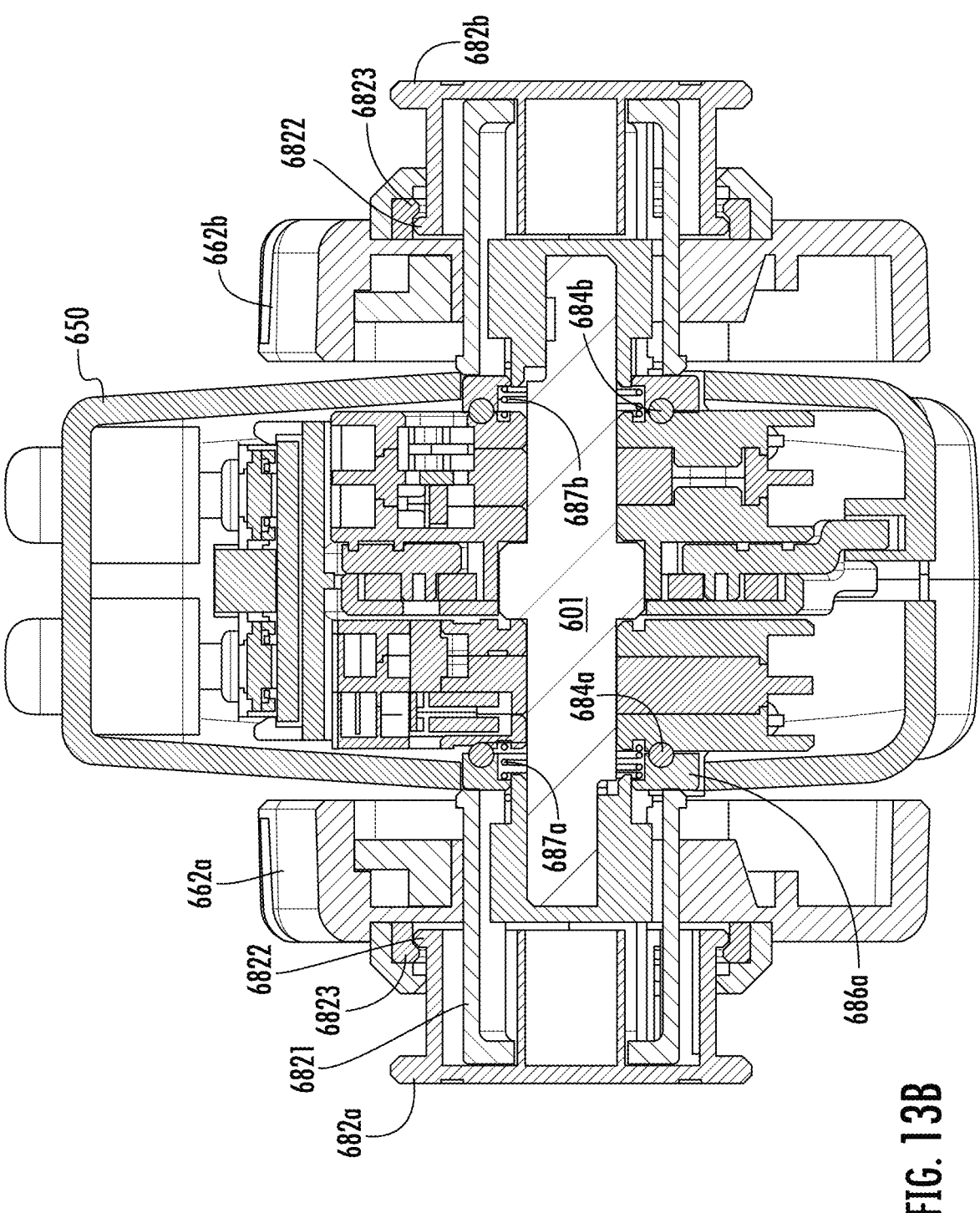

FIGS. 13A and 13B are rear cross-sectional views of the handle 650 showing additional features thereof, and showing the steering wire braking mechanisms 682a, 682b respectively disengaged and engaged. For example, FIG. 13A shows the components of the shaft steering system 656 in a disengaged, e.g., unlocked, configuration. As shown in FIG. 13A, the steering wire braking mechanisms 682a, 682b are located relative to the first and second roller wheels 600a, 600b at a first, e.g., more radially spaced, position. In this first position, the fingers 6821 of the steering wire braking mechanisms 682a, 682b are engaged with but not pressing the o-ring retention members 686a, 686b radially inwardly sufficiently to overcome the biasing force of the springs 687a, 687b against the interior annular lips 685a, 685b of the o-ring retention members 686a, 686b. Thus, the springs 687a, 687b push the o-ring retention members 686a, 686b radially outward such that the o-rings 684a, 684b are spaced apart from the radially outer side of the first and second roller wheels 600a, 600b. Because the o-rings 684a, 684b are spaced apart from the radially outer sides of the first and second roller wheels 600a, 600b, there is little or no frictional force created between the o-rings 684a, 684b and the first and second roller wheels 600a, 600b, and thus the first and second roller wheels 600a, 600b are relatively free to rotate within the handle 650 and their respective steering wires are able to be steered. Of course, it should be recognized that, while this feature is described above in connection with the first and second roller wheels 600a, 600b that control left and right movement of the distal end of the shaft, the other rollers wheels described herein, e.g., the roller wheels that control up and down movement of the distal end of the shaft, may function similarly and thus enjoy the same benefits.

FIG. 13B, on the other hand, shows the components of the shaft steering system 656 in an engaged, e.g., locked, configuration. As shown in FIG. 13B, the steering wire braking mechanisms 682a, 682b are located relative to the first and second roller wheels 600a, 600b at a second, e.g., less radially spaced, position. In this second position, the fingers 6821 of the steering wire braking mechanisms 682a, 682b are pressing the o-ring retention members 686a, 686b radially inwardly sufficiently to overcome the biasing force of the springs 687a, 687b against the interior annular lips 685a, 685b of the o-ring retention members 686a, 686b. Thus, the force of the springs 687a, 687b is overcome such that the finger 6821 of the steering wire braking mechanism 682a, 682b push the o-ring retention members 686a, 686b radially inward until the o-rings 684a, 684b are no longer spaced apart from, but rather are touching or pressing against, the radially outer side of the first and second roller wheels 600a, 600b. Because the o-rings 684a, 684b are pressing against the radially outer sides of the first and second roller wheels 600a, 600b, there is a frictional force created between the o-rings 684a, 684b and the first and second roller wheels 600a, 600b, and thus the first and second roller wheels 600a, 600b are braked, e.g., prevented or limited from rotating, within the handle 650 and likewise, their respective steering wires are prevented or reduced from further movement to thereby maintain the shaft, e.g., the distal tip, in a particular desired position.

Various mechanisms are contemplated in order to maintain the o-rings 684a, 684b pressing against the radially outer sides of the first and second roller wheels 600a, 600b so as to create the frictional force between the o-rings 684a, 684b and the first and second roller wheels 600a. For example, and as shown in FIGS. 13A through 13D, the system may also include brake holding mechanisms. In the embodiment shown in FIGS. 13A and 13B, the brake holding mechanism includes an annular ring 681a, 681b housing an annular lip 6823 on respective outer sides of the first and second roller knobs 662a, 662b. In addition, the brake holding mechanism includes annular rings 6822 on an external circumferential surface of steering wire braking mechanisms 682a, 682b. The annular rings 681a, 681b on the outer sides of the first and second roller knobs 662a, 662b engage annular lips 6822 on the external circumferential surfaces of steering wire braking mechanisms 682a, 682b so as to selectively lock (and unlock) the position of the steering wire braking mechanisms 682a, 682b relative to the first and second roller knobs 662a, 662b, and consequently lock (and unlock) the o-rings 684a, 684b in frictional engagement against the radially outer sides of the first and second roller wheels 600a, 600b. In embodiments, one or both of the annular lips 6822, 6823 may be flexible lips that, when the steering wire braking mechanisms 682a, 682b are pressed radially inwardly, the lips 6822, 6823 flex to allow relatively movement therebetween but have sufficient rigidity to maintain the position. In such an embodiment, the brake holding mechanisms are actuated via pushing or pulling the steering wire braking mechanisms 682a, 682b relative to the first and second steering knobs 662a, 662b.

Figure 13C:
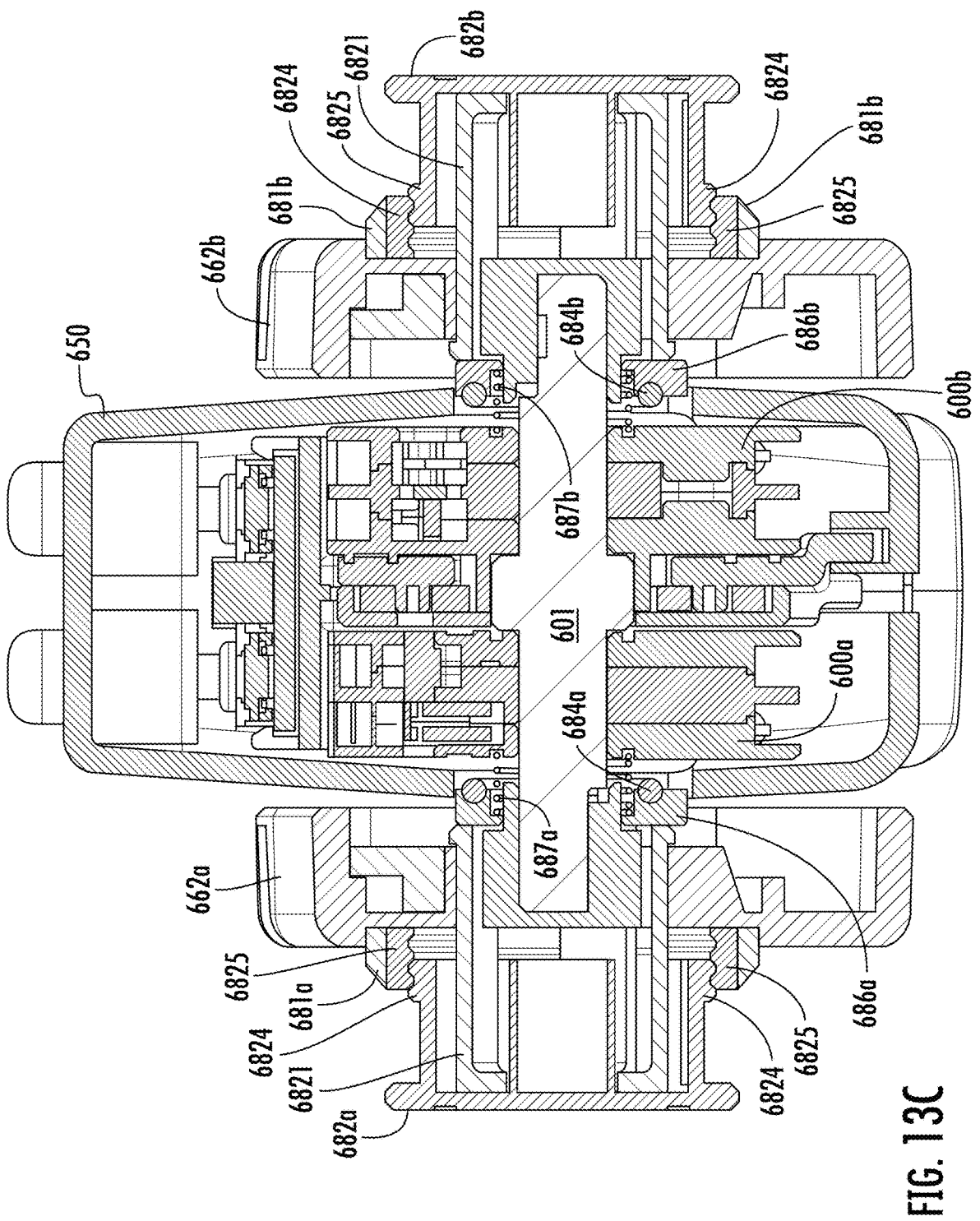
Figure 13D:
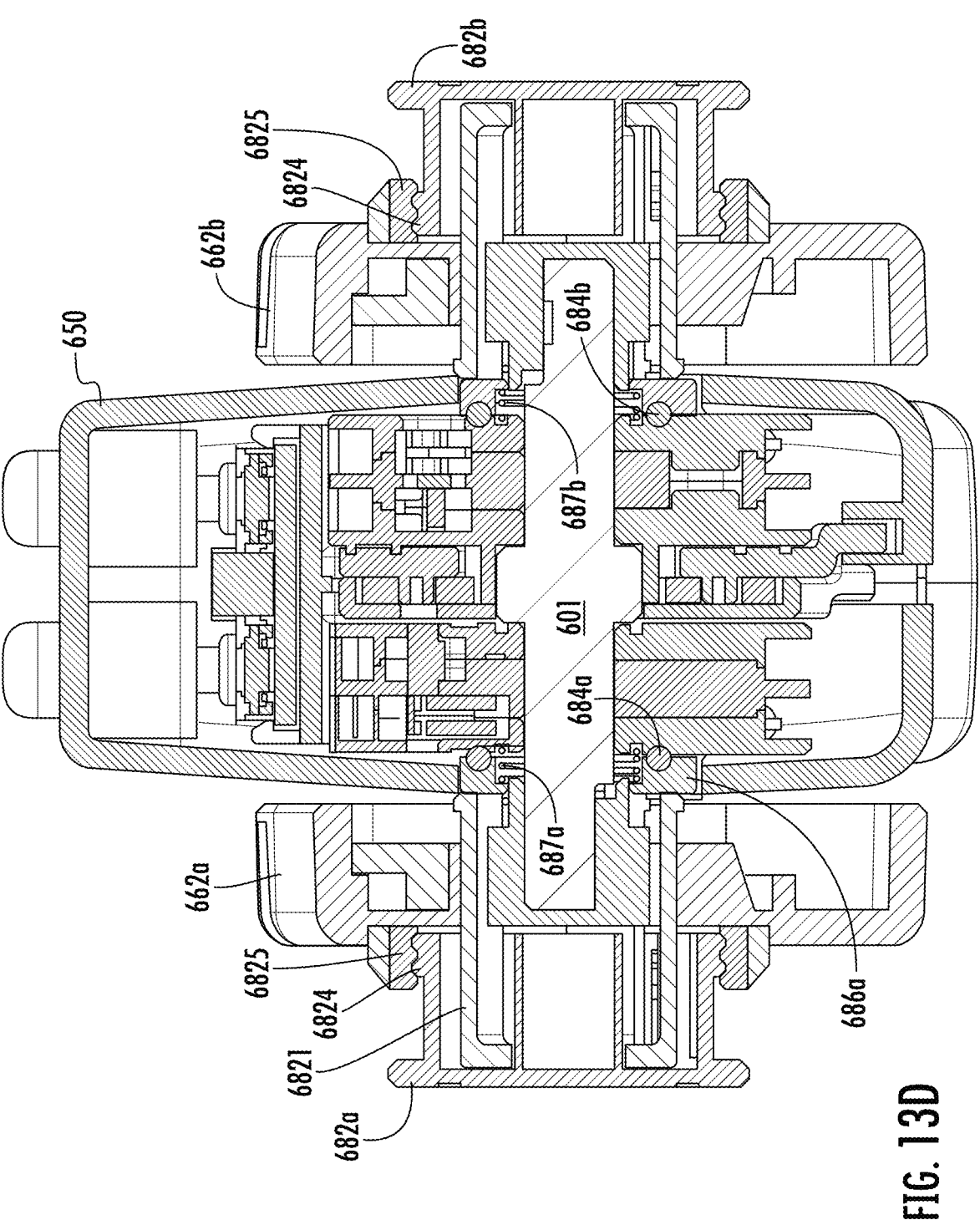

Alternatively, as shown in FIGS. 13C and 13D, the annular lips on respective outer sides of the first and second roller knobs 662a, 662b and on an external circumferential surface of steering wire braking mechanisms 682a, 682b may constitute annular threads 6824, 6825, respectively. In this case, the threads 6825 on the outer sides of the first and second roller knobs 662a, 662b engage the threads 6824 on the external circumferential surfaces of steering wire braking mechanisms 682a, 682b so as to selectively lock (and unlock) the position of the steering wire braking mechanisms 682a, 682b relative to the first and second roller knobs 662a, 662b, and consequently lock (and unlock) the o-rings 684a, 684b in frictional engagement against the radially outer sides of the first and second roller wheels 600a, 600b. In such an embodiment, the brake holding mechanisms may be actuated via rotating the steering wire braking mechanisms 682a, 682b relative to the first and second steering knobs 662a, 662b, and may have the advantage that the degree of friction (and thus the degree of locking) may be well controlled by the user.

Maintaining the shaft, e.g., the distal tip, in a desired position may have various advantages. For example, if the shaft, e.g., distal tip, moves after the user has placed it into a desired position, the illumination device and/or camera located at the distal tip may no longer be pointed at the specific anatomical feature of the patient which is desired to be focused on. If the illumination device and/or camera located at the distal tip is no longer pointed at the specific anatomical feature of the patient which is desired to be focused on, the surgeon may not see critical structures and/or be able to observe the distal tip fully, which may result in the need for the surgeon to adjust the distal tip again to return it to the desired position, wasting valuable surgical time. Also, if the surgeon is unable to see critical structures and/or be able to observe the distal tip fully because the illumination device and/or camera is no longer pointed at the desired location, the risk that a surgeon makes an error during surgery—e.g., because she is unable to see how the distal tip of the shaft is interacting with the critical anatomical structures within the patient—may be increased. In contrast, the steering tension braking feature, by preventing the shaft from inadvertently or unintentionally moving after a desired steered position has been achieved, may help reduce or eliminate such risk by ensuring that the illumination device and/or camera located at the distal tip remains pointed at the specific anatomical feature of the patient which is desired to be focused on so that the surgeon may see critical structures and/or be able to observe the distal tip more fully during surgery.

Still further, if the shaft, e.g., distal tip, moves after the user has placed it into a desired position, the movement of the shaft itself, independent of engagement by the surgeon, may also inadvertently injure the soft tissues within the patient. For example, the spaces into which the shaft is inserted are small and narrow, and typically formed by delicate soft tissue, and the surgeon typically takes great care in order to place the distal tip into a desired resting position at which the distal tip is not pressing against or touching critical soft tissues. If the distal tip moves away from this position, e.g., due to the internal or external forces that are exerted thereon as described above, the distal tip (or other parts of the shaft) may touch or press into these critical soft tissues and thereby increase the risk that these critical soft tissues are undesirably touched, harmed or injured. In contrast, the steering tension braking feature, by preventing the shaft from inadvertently or unintentionally moving after a desired steered position has been achieved, may help reduce or eliminate such risk by ensuring that the distal tip does not inadvertently move, e.g., after the surgeon has placed the distal tip into a desired resting position, into an unintended subsequent position at which the distal tip is pressing against or touching critical soft tissues.

In embodiments, in addition to the various steering wire tensioning mechanisms described hereinabove, the steering control mechanisms may also include a steering wire slack reduction feature. This steering wire slack reduction feature may prevent or at least reduce unintended slack from forming along the steering wires during use. For example, friction along the steering wires—such as may result from the steering wires travelling over or through guide locations etc.—may occur as the steering wires are operated by a user. This friction along the steering wires may cause the steering wires to slacken in various locations, and this slackening may cause the steering wires to jump out of one or more of their respective guides and/or to get caught up on other structures within the handle, any one of which may result in the endoscopy device malfunctioning, e.g., being unable to steer or other problems. Likewise, this unintended slackening may cause the steering wire to feel or move jerkingly or otherwise unpredictably to the user while in use, potentially causing the user to move the shaft imprecisely and/or not smoothly. The steering wire slack reduction feature may help alleviate or eliminate these problems by keeping some additional tension on the steering wires while they are being operated by the user.

Figure 14:
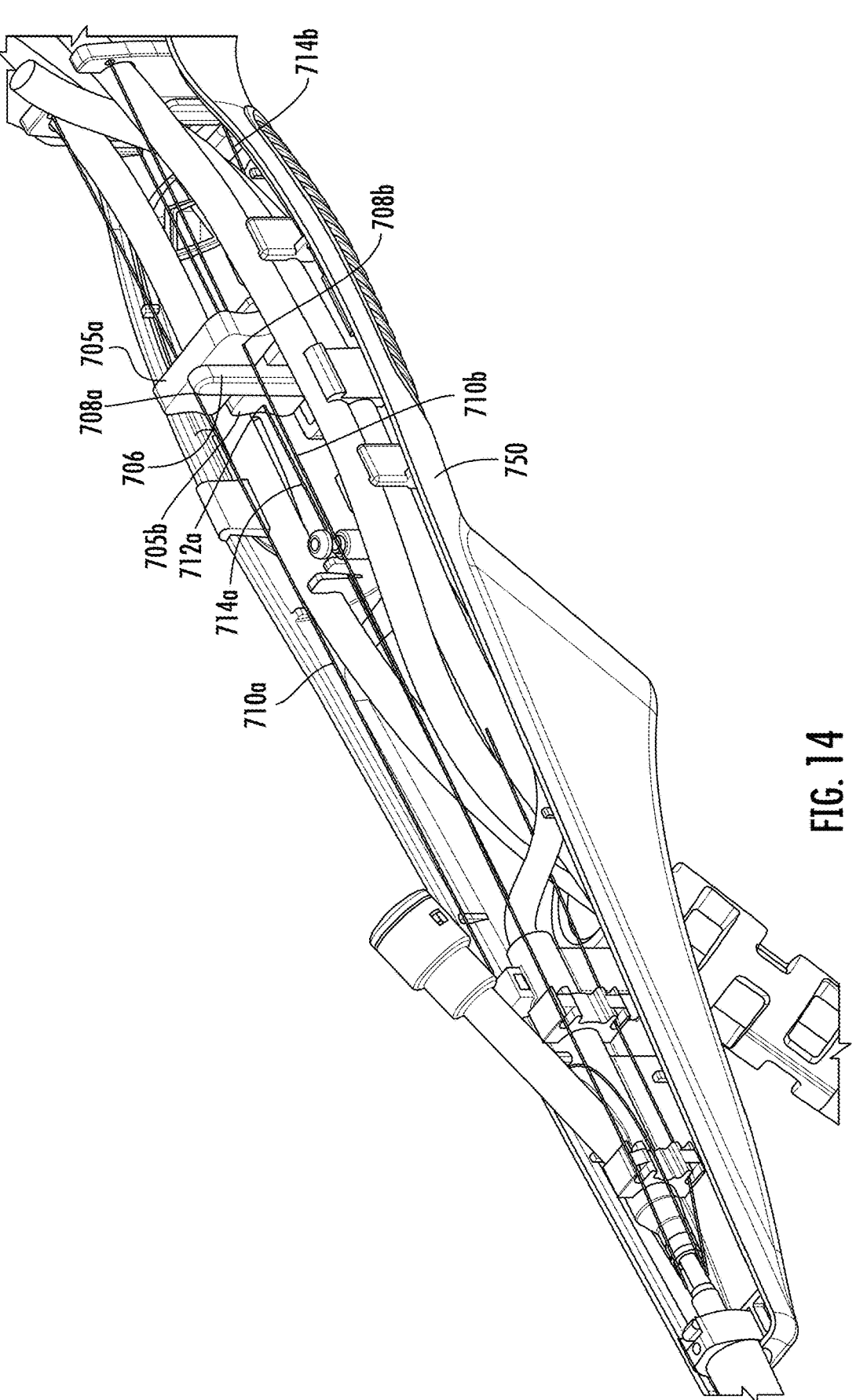
FIG. 14 is a side perspective view of a handle having the upper shell portion removed so as to illustrate slack reduction members mounted within the handle, in accordance with various embodiments.

In certain embodiments, the steering wire slack reduction feature may include a slack reduction member. For example, FIG. 14 is a side perspective view of a handle 750 having portions, e.g., the upper shell portion, of the handle removed so as to show the interior thereof. FIG. 14 illustrates slack reduction members 705*a*, 705*b* mounted within the handle 750, it being recognized that while two such slack reduction members are shown in this embodiment, any number of such members, e.g., a single member or more than two members, are contemplated. In the embodiment shown, both of the slack reduction members 705*a*, 705*b* are mounted on a post 706 within the handle 750. The post 706 may be molded integrally with the handle 750, or the post 706 may be separately molded and mounted therewithin. Of course, other structures besides a post 706, e.g., fingers, nubs or other protuberances, may be employed to mount or maintain the slack reduction members 705*a*, 705*a* within the handle 750. In embodiments, the slack reduction member, e.g., slack reduction members 705*a*, 705*b*, are formed of a flexible material. The flexible material may be, e.g., silicone, although other flexible materials are also contemplated.

In the embodiment shown in FIG. 14, each one of the slack reduction members 705*a*, 705*b* supports and engages a pair of steering wires. For example, in an embodiment, the slack reduction member 705*a* includes a pair of through-holes 708*a*, 708*b* through which steering wires 710*a*, 710*b*, respectively extend. Likewise, the slack reduction member 705*b* includes a pair of through-holes 712*a* (and a second through-hole 712*b* which is hidden in this view) through which steering wires 714*a*, 714*b*, respectively extend. Of course, different numbers of steering wires may extend through the slack reduction members, depending on the number of steering wires employed in a given endoscope design.

In this embodiment, each of the through-holes and steering wires are complementary sized relative to each other. For example, the through-holes 708*a*, 708*b* and the steering wires 710*a*, 710*b* are complementary sized such that the steering wires 710*a*, 710*b* may slide through, advantageously while still experiencing some frictional engagement with, the side walls of the through-holes 708*a*, 708*b*. The sizing is such that frictional engagement between the respective steering wires 710*a*, 710*b* and the through-holes 708*a*, 708*b* is sufficient to allow relatively easy sliding therethrough, with just enough frictional engagement to maintain a gentle tension on the steering wires 710*a*, 710*b* and prevent them from slackening during use. Likewise, the through-holes 712*a*, 712*b* and the steering wires 714*a*, 714*b* are complementary sized such that the steering wires 714*a*, 714*b* may slide through, while still experience some frictional engagement with, the side walls of the through-holes 712*a*, 712*b*. Again, the sizing is such that frictional engagement between the respective steering wires 714*a*, 714*b* and the through-holes 712*a*, 712*b* is sufficient to allow relatively easy sliding therethrough, with just enough frictional engagement to maintain a gentle tension on the steering wires 714*a*, 714*b* and prevent them from slackening during use.

It should be recognized that alternative steering wire slack reduction feature designs are also contemplated. For example, while the steering wire slack reduction feature described above and shown in FIG. 14 has steering wires that slide through respective through-holes of the slack reduction members 705*a*, 705*b*, other arrangements are contemplated in which the steering wires slide relative to other features of the slack reduction members 705*a*, 705*b*. For example, in such an embodiment, the through-holes of the slack reduction members 705*a*, 705*b* may be replaced by, e.g., slits, indentations or other voids through which the steering wires may slide.

Furthermore, while the steering wire slack reduction feature described above and shown in FIG. 14 has steering wires that slide relative to the slack reduction members 705*a*, 705*b* and which rely on frictional engagement therebetween to reduce potential slackness of the steering wires, other arrangements are contemplated in which the steering wires do not slide relative to the slack reduction members 705*a*, 705*b*. For example, in some embodiments, the steering wires may be attached to the slack reduction members 705, 705*b*, and the slack reduction may result from the flexibility of the slack reduction members 705*a*, 705*b*. In other words, in such embodiments, steering wires may pass through through-holes (or over or alongside edges of) the slack reduction members 705*a*, 705*b* but rather than sliding relative thereto, the steering wires may be attached, e.g., connected, glued, molded, etc., thereto. In this case, the slack reduction members 705*a*, 705*b* may flex longitudinally within the handle as the steering wires are moved, with the resiliency of the slack reduction members 705*a*, 705*b* providing tension on the steering wires as the slack reduction members flex forward and backwards.

Still further, while the above-described steering wire slack reduction feature includes slack reduction members 705*a*, 705*b* that flex longitudinally, e.g., backwards and forwards, within the handle as the steering wires are moved, other arrangements in which the slack reduction members 705*a*, 705*b* flex in different ways, are also contemplated. For example, in some embodiments, the steering wires may engage, e.g., either slidably or non-slidably, with the slack reduction members 705, 705*b*, and the slack reduction may result from the radial resiliency of the slack reduction members 705*a*, 705*b*. In other words, in such embodiments, steering wires may pass through through-holes (or over or alongside edges of) the slack reduction members 705*a*, 705*b* but rather than the slack reduction members 705*a*, 705*b* flexing longitudinally, the slack reduction members 705*a*, 705*b* may flex radially as the steering wires are tensioned by pulling, with the resiliency of the slack reduction members 705*a*, 705*b* providing additional tension on the steering wires. Conversely, as the tension on the steering wires is reduced, e.g., by the user no longer pulling on them, the resiliency of the slack reduction members 705*a*, 705*b* may cause them to flex radially outwardly to their original unflexed position, thereby maintaining some additional tension on the steering wires.

As set forth above, a steering wire slack reduction feature may provide several advantages. For example, as a steering wire is operated by a user, friction that is experienced by the steering wires as they pass over or through guide locations may cause the steering wires to slacken, and thereby jump out of one or more of their respective guides and/or to get caught up on other structures within the handle. The slack reduction features, as described hereinabove, may help prevent an endoscopy device malfunctioning in this way by providing additional tension to the steering wires during use and thereby reducing unintended slack from forming along the steering wires during use. Likewise, the slack reduction features, as described hereinabove, may help prevent the steering wires from jerking or otherwise moving unpredictably while in use, enabling the user to move the shaft more precisely and/or smoothly. The additional precision and smoother movements during use helps ensure a more predictable surgical outcome, reducing the likelihood of surgeon frustration and/or error and reducing the risk of patient injury.

There are no limitations in terms of the particular embodiments described in this application, which are intended as illustrations of various aspects only. Many modifications and variations can be made without departing from its spirit and scope, as will be apparent to those skilled in the art. Functionally equivalent methods and apparatuses, in addition to those enumerated herein, will be apparent to those skilled in the art from the foregoing descriptions. Such modifications and variations are intended to fall within the scope of the appended claims. Only the terms of the appended claims are intended to be limiting, along with the full scope of equivalents to which such claims are entitled. It is also to be understood that the terminology used herein, e.g., "and", "or", "including", "at least" as well as the use of plural or singular forms, etc., is for the purpose of describing examples of embodiments and is not intended to be limiting.

What is claimed is:

1. An endoscope for use in a surgical procedure, comprising:

a handle for gripping by a user, the handle having a steering control mechanism;

a shaft extending from the handle, the shaft having a distal region configured to be inserted into a patient;

a steering wire extending longitudinally through the shaft from the distal region of the shaft to the steering control mechanism of the handle, the steering control mechanism including a roller knob located outside of the handle and a roller wheel located within the handle and attached to the steering wire, the roller knob and roller wheel rotatable about an axis through the handle and actuatable by a user during the surgical procedure to generate a steering tension force on the steering wire so as to steer the distal region of the shaft; and the steering control mechanism including a steering wire brake that projects beyond the roller knob in a direction of the axis and that, upon the user pushing or pulling the steering wire brake relative to the roller knob in the direction of the axis, frictionally engages the roller wheel within the handle so as to brake the steering tension force on the steering wire, wherein the steering wire brake is selectively lockable and unlockable via a brake lock that includes a flexible annular lip that engages a complementary annular lip on the handle.

2. The endoscope of claim 1, wherein the steering wire brake prevents the shaft from moving after a desired steered position has been achieved.

3. The endoscope of claim 1, wherein the steering wire brake includes an o-ring selectively pressable into the roller wheel within the handle, the steering wire attached to and actuatable by the roller wheel.

4. The endoscope of claim 3, wherein the o-ring resides within an o-ring retention member that is movable radially inwardly and outwardly relative to the handle.

5. The endoscope of claim 4, wherein the steering wire brake includes a user-actuatable button having a radially-inwardly extending finger that engages the o-ring retention member.

6. The endoscope of claim 5, wherein the o-ring retention member is biased radially outwardly by a spring such that, in a resting position when the button is not pressed, the spring maintains the o-ring spaced apart from the roller wheel such that the steering wire is not braked.

7. The endoscope of claim 6, wherein, in an actuated position with the button pressed, a force of the spring maintains is overcome such that the o-ring presses against the roller wheels such that the steering wire is braked.

* * * * *